(12) United States Patent
Otawara

(10) Patent No.: US 8,114,013 B2
(45) Date of Patent: Feb. 14, 2012

(54) ENDOSCOPE INSERTION PORTION

(75) Inventor: Takashi Otawara, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1259 days.

(21) Appl. No.: 11/825,077

(22) Filed: Jul. 3, 2007

(65) Prior Publication Data
US 2008/0177144 A1 Jul. 24, 2008

Related U.S. Application Data

(63) Continuation of application No. PCT/JP2006/300271, filed on Jan. 12, 2006.

(30) Foreign Application Priority Data

Jan. 17, 2005 (JP) ................................. 2005-009473

(51) Int. Cl.
A61B 1/04 (2006.01)
A61B 1/06 (2006.01)
A61B 1/015 (2006.01)

(52) U.S. Cl. ........ 600/129; 600/130; 600/157; 600/168; 600/176

(58) Field of Classification Search .................. 600/129, 600/130, 157, 168, 176, 182
See application file for complete search history.

(56) References Cited

U.S. PATENT DOCUMENTS

| 4,667,656 A * | 5/1987 | Yabe ............................. 600/109 |
| 5,445,157 A * | 8/1995 | Adachi et al. ................. 600/474 |
| 5,782,751 A * | 7/1998 | Matsuno ....................... 600/157 |
| 6,217,510 B1 | 4/2001 | Ozawa et al. |
| 6,641,530 B2 * | 11/2003 | Mitsumori .................... 600/167 |
| 2004/0122290 A1 * | 6/2004 | Irion et al. .................... 600/171 |
| 2004/0156124 A1 | 8/2004 | Okada |
| 2004/0158129 A1 | 8/2004 | Okada et al. |

FOREIGN PATENT DOCUMENTS

| JP | HEI 1-133901 | 9/1989 |
| JP | 05-297288 | 11/1993 |
| JP | 06-154155 | 6/1994 |
| JP | 8-89474 | 4/1996 |
| JP | 9-220192 | 8/1997 |
| JP | 11-104070 | 4/1999 |
| JP | 2003 310543 A | 11/2003 |
| JP | 2004-240346 | 8/2004 |

OTHER PUBLICATIONS

Translation of JP 06-154155-A, Jun. 1994.*
Official Action dated Oct. 27, 2009.

* cited by examiner

Primary Examiner — John P Leubecker
(74) Attorney, Agent, or Firm — Scully, Scott, Murphy & Presser, P.C.

(57) ABSTRACT

An endoscope insertion portion capable of illuminating a diseased part corresponding to a part of an endoscope image by irradiation light in an amount approximately the same as that in non-enlarged display, when displaying the part of the endoscope image in an enlarged manner. The endoscope insertion portion of this invention includes: an insertion portion having a distal end surface; a first illumination optical system for irradiating light onto a subject; a second illumination optical system for irradiating light onto the subject; a first image pickup portion including on the distal end surface a first optical member for introducing light from the subject; and a second image pickup portion including a second optical member for introducing light from the subject, the second optical member being disposed in an area sandwiched by the first illumination optical system and the second illumination optical system.

7 Claims, 13 Drawing Sheets

ENDOSCOPE INSERTION PORTION

CROSS REFERENCE TO RELATED APPLICATION

This application is a continuation application of PCT/JP2006/300271 filed on Jan. 12, 2006 and claims benefit of Japanese Application No. 2005-009473 filed in Japan on Jan. 17, 2005, the entire contents of which are incorporated herein by this reference.

BACKGROUND OF THE INVENTION

1. Field of the Invention

The present invention relates to an endoscope insertion portion including a first image pickup portion and a second image pickup portion having a higher observation magnification compared to the first image pickup portion.

2. Description of the Related Art

Conventionally, the endoscope has been widely used in a medical field, and the like. The endoscope, for example, can provide observation of an organ and the like within a body cavity by inserting an elongated insertion portion into the body cavity as a subject, and various treatments using a treatment instrument inserted into a treatment instrument insertion channel as needed. A bending portion is provided at a distal end of the insertion portion, so that an observation direction of an observation window at a distal end portion can be changed by operating an operation portion of the endoscope.

As the endoscope described above, for example, Japanese Unexamined Patent Application Publication No. 06-154155 proposes the endoscope including in the distal end portion of the insertion portion a first objective optical system and a second objective optical system as observation optical systems and an illumination optical system for emitting illumination light supplied from a light source device as an illumination portion to a subject, and solid image pickup devices as image pickup devices corresponding to the respective objective optical systems at image forming positions of the first objective optical systems and the second objective optical systems.

SUMMARY OF THE INVENTION

An endoscope insertion portion of the present invention comprises: an insertion portion including a distal end surface; a first illumination optical system for irradiating light onto a subject, the first illumination optical system being disposed on the distal end surface; a second illumination optical system for irradiating light onto the subject, the second illumination optical system being disposed on the distal end surface; a first image pickup portion including a first optical member for introducing light from the subject, the first optical member being provided on the distal end surface; and a second image pickup portion having a higher observation magnification than that of the first image pickup portion, including a second optical member for introducing light from the subject, the second optical member being disposed in an area sandwiched between the first illumination optical system and the second illumination optical system.

DETAILED DESCRIPTION OF THE PREFERRED EMBODIMENT(S)

Below, embodiments of the present invention will be described with reference to the drawings.

Figure 1:
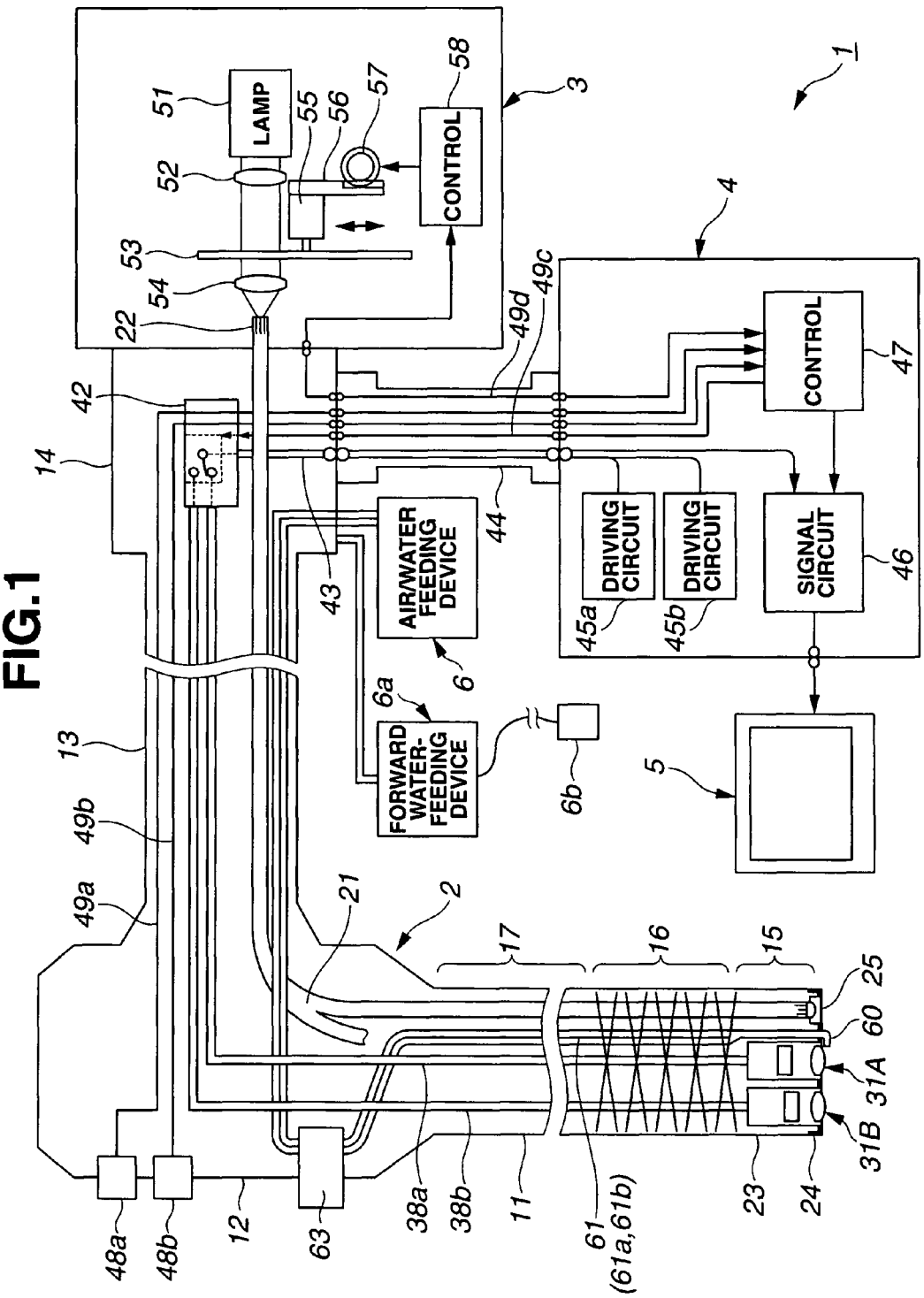
FIG. 1 is an explanatory view schematically showing an endoscope system according to an embodiment of the present invention.

First, a configuration of an endoscope system according to an embodiment of the present invention will be described based on FIG. 1. FIG. 1 is an explanatory view schematically showing the endoscope system according to the embodiment of the present invention.

As shown in FIG. 1, an endoscope system 1 according to a first embodiment of the present invention includes in the present embodiment: an endoscope 2 capable of performing a normal light observation and a fluorescent light observation; a light source device 3 for supplying illumination light to the endoscope 2; a processor 4 serving as a signal processing device for performing signal processing with respect to the endoscope 2 having an endoscope insertion portion; a monitor 5 serving as a display portion for displaying endoscope images for the normal light observation and the fluorescent light observation in response to a video signal outputted from the processor 4 and inputted to the monitor; an air/water feeding device 6 for feeding air or water; and a forward water-feeding device 6a for feeding water forward.

The endoscope 2 includes an elongated insertion portion 11 for easier insertion into a body cavity as a subject, an operation portion 12 linked to a proximal end of the insertion portion 11, and a universal cable 13 extended from a side portion of the operation portion 12. A connector 14 provided at an end portion of the universal cable 13 is detachably connected to the light source device 3.

In addition, the insertion portion 11 of the endoscope 2 has a configuration as an endoscope insertion portion, and includes a rigid distal end portion 15 formed at a distal end thereof, a bending portion 16 formed at a proximal end of the distal end portion 15, and a flexible tube portion 17 having a flexibility formed from a proximal end of the bending portion 16 to the operation portion 12.

In the insertion portion 11, a light guide 21 for transmitting illumination light is inserted. The light guide 21 is inserted in the universal cable 13 via the operation portion 12 to be connected to a light guide connector, not shown, of which proximal end portion 22 is projected out from the connector 14.

In addition, a distal end part of the light guide 21 is fixed in the distal end portion 15. Note that, at a distal end part of the distal end portion 15, an illumination lens 25 of an illumination unit to be described later serving as an illumination optical system is provided and illumination light is emitted from the light guide 21 via the illumination lens 25. Furthermore, on a distal end surface of the distal end portion 15, a distal end cover 24 is provided.

Note that, in the present embodiment, the light guide 21 diverges in the operation portion 12, for example, and inserted in the insertion portion 11, divided into two parts. Then, distal end surfaces of the respective divided two parts of the light guide 21 are arranged in the vicinity of rear surfaces of the two illumination lenses 25 provided on the distal end cover 24, respectively.

Moreover, though illustration is omitted in FIG. 1, the insertion portion 11 has inside thereof a treatment instrument channel (also referred to as a forceps channel) as a first duct for allowing a treatment instrument such as a forceps to be inserted, for example. The distal end of the treatment instrument channel is open on a distal end surface of the distal end cover 24.

The treatment instrument channel diverges in the vicinity of a proximal end side of the insertion portion 11. One diverging part of the treatment instrument channel is inserted to reach a treatment instrument insertion port, not shown, provided on the operation portion 12. In addition, the other diverging part of the treatment instrument channel passes through the insertion portion 11 and the universal cable 13 to communicate with a suction channel, and proximal end of the diverging part is connected to a suction means, not shown, via the connector 14.

Two image pickup units are provided in the distal end portion 15. In the present embodiment, a normal-light-observing image pickup unit (hereinafter referred to as a normal light image pickup unit) 31A which is an image pickup portion for normal light observation, and a fluorescent-light-observing image pickup unit (hereinafter referred to as a fluorescent light image pickup unit) 31B which is an image pickup portion for special light observation are incorporated.

Note that, in the present embodiment, the image pickup portion for the special light observation, described above, is the fluorescent-light-observing image pickup unit capable of performing fluorescent light. However, the image pickup portion is not limited especially to the unit for fluorescent light observation, and may be, for example, a night vision-observing image pickup unit, an infrared-light-observing image pickup unit, or the like.

In addition, in the present embodiment, a tele-zoom operation is possible in the normal light image pickup unit 31A as described later, the normal light image pickup unit 31A can obtain an image of the subject with a higher observation magnification compared with the fluorescent light image pickup unit 31B.

To the normal light image pickup unit 31A and the fluorescent light image pickup unit 31B, one ends of signal cables 38*a*, 38*b* are connected, respectively. The other ends of the signal cables 38*a*, 38*b* are inserted in the operation portion 12 and the universal cable 13, and switchably connected to a common signal cable 43 on a relay substrate 42 provided in the connector 14.

The common signal cable 43 is connected to the processor 4 by passing through in a scope cable 44 which is connected to the connector 14.

The processor 4 has inside thereof, driving circuits 45*a*, 45*b* which drive the normal light image pickup unit 31A and the fluorescent light image pickup unit 31B, respectively, a signal processing circuit 46 for performing signal processing on the image pickup signals outputted respectively from the two image pickup devices via the relay substrate 42, and a control circuit 47 for controlling operation states of the signal processing circuit 46 and the like.

In addition, the operation portion 12 of the endoscope 2 includes control switches 48*a*, 48*b*, an air/water feeding button 63, a bending operation knob, not shown, a switch (also referred to as a tele-zoom button), not shown, for performing tele-zoom operation of the normal light image pickup unit 31A, a forward water-feeding button, not shown, and the above-described treatment instrument insertion port, not shown.

The control switches 48*a*, 48*b* are connected to the control circuit 47 of the processor 4 via signal lines 49*a*, 49*b*, respectively. In the present embodiment, the control switch 48*a* generates a switching instruction signal, for example, and the control switch 48*b* generates a freeze instruction signal, for example.

The relay substrate 42 performs a switching operation so as to switch from a state where one of the signal cables 38*a*, 38*b* which are connected to the image pickup devices respectively is connected to the common signal cable 43 to a state the other cable is connected to the signal cable 43, in response to an operation of the control switch 48*a*, for example.

Specifically, when the control switch 48*a* is operated, for example, a switching signal is outputted to the relay substrate 42 via a switching signal line 49*c* inserted in the scope cable 44 and electrically connected to the control circuit 47. The relay substrate 42, to which a switching signal line 49*c* is connected, is in a state where an input terminal to which a signal is inputted from the control circuit is normally in an L (LOW) level and a switching control terminal is pulled down. In this state, the signal cable 38*a* of the normal light image pickup unit 31A is connected to the common signal cable 43. In addition, also in a case of activation start state, the switching control terminal is set to be in the low level. That is, the switching control terminal of the relay substrate 42 is set to be for the normal light observation, unless switching instruction operation is performed.

When a user operates the control switch 48*a* in this state, a control signal is applied from the control circuit 47 via the switching signal line 49*c* to the input terminal of the relay substrate 42 such that the level of the input terminal becomes H (HIGH) level, and the switching control terminal of the relay substrate 42 is pulled up. Then, in the state, the signal cable 38*b* of the fluorescent light image pickup unit 31B is connected to the common signal cable 43.

In addition, when the user operates the control switch 48*a* in the above-described state, a control signal is applied from the control circuit 47 via the switching signal line 49*c* to the input terminal of the relay substrate 42 such that the level of the input terminal becomes L level, and the switching control terminal is pulled down. Then, in the state, the signal cable 38*a* of the normal light image pickup unit 31A is connected to the common signal cable 43.

In addition, in response to the operation of the control switch 48*a*, the control circuit 47 outputs a control signal also to a control circuit 58 in the light source device 3 via a control signal line 49d in the scope cable 44. Then, the control circuit 58 controls the respective portions of the light source device 3 such that normal observation light or excitation light for fluorescent light observation can be generated in response to the control signal outputted from the control circuit 47. Furthermore, the control circuit 47 causes the respective image pickup devices of the normal light image pickup unit 31A and the fluorescent light image pickup unit 31B to perform corresponding operations by controlling an operation state of the signal processing circuit 46.

The light source device 3 as an illumination portion includes a lamp 51 for generating white light including a wavelength of excitation light, a collimator lens 52 for rendering the light of the lamp 51a parallel light flux, a rotation filter 53 which is disposed in an optical path of the collimator lens 52 and includes in a circuit direction thereof an RGB filter for transmitting respective wavelength components of R (RED), G (GREEN) and B (BLUE) in a visible light wavelength band (from 380 nm to 780 nm), for example, and a condenser lens 54 for condensing light transmitted through the rotation filter 53 to emit the light to a proximal end portion 22 of the light guide 21.

In addition, the rotation filter 53 provided with the RGB filter has outside of the circuit direction an excitation light filter for transmitting the excitation light of a wavelength band shorter than that of visible light. The rotation filter 53 is rotated and driven by a motor 55. Moreover, the motor 55 is mounted to a rack 56 and configured to move in a direction orthogonal to an illumination optical axis by a gear-equipped motor 57 engaged with the rack 56, as shown by an arrow.

The gear-equipped motor 57 is controlled by a control circuit 58. The control circuit 58 is connected with the control circuit 47 of the processor 4 via the control signal line 49d and performs control action in response to an operation of the control switch 48a.

In addition, at the distal end portion 15, an air/water feeding nozzle 60 serving as an air/water feeding portion is disposed such that a spouting port thereof faces outer surfaces of the respective objective lenses (later, also referred to as observation lenses) of the normal light image pickup unit 31A and the fluorescent light image pickup unit 31B which are disposed on the distal end cover 24.

The air/water feeding nozzle 60 is, as described later, connected to an air/water feeding duct 61 configured to be diverged at a proximal end thereof into two ducts of an air feeding duct 61a and a water feeding duct 61b, and integrated at a distal end thereof into one duct with the two ducts merged.

The air feeding duct 61a and the water feeding duct 61b which are communicating with the air/water feeding nozzle 60 are inserted to reach the connector 14 of the universal cable 13, and connected to the air/water feeding device 6 incorporating a pump, not shown, for feeding air and water.

The air feeding duct 61a and the water feeding duct 61b are interposed with the air/water feeding button 63 in the operation portion 12 located at halfway of the ducts. Then, air and water are fed by operating the above-described air/water feeding button 63.

This allows the air/water feeding nozzle 60 to spray gas such as air or liquid such as distilled water to the outer surfaces of the respective objective lenses of the normal light image pickup unit 31A and the fluorescent light image pickup unit 31B disposed in a spouting direction of the air or liquid, to clean and remove body fluid, extraneous matter, or the like, thereby ensuring an image pickup and an observation field of view in a clean state.

Although omitted in FIG. 1, the insertion portion 11 has inside thereof a forward water-feeding channel as a second duct for feeding liquid such as distilled water to a region to be inspected in a body cavity. And the distal end of the forward water-feeding channel opens on a distal end surface of the distal end cover 24.

The forward water-feeding channel is connected to the forward water-feeding device 6a, and has a forward water-feeding button not shown provided in the operation portion 12. When the forward water-feeding button is operated, liquid such as distilled water is sprayed from the distal end surface of the insertion portion 11 in an insertion direction into the body cavity. This allows the body fluid and the like attached to the region to be inspected in the body cavity to be cleaned. Note that, as shown in FIG. 1, a foot switch 6b is connected to a cable extending from the forward water-feeding device 6a, therefore a user can spray liquid such as distilled water from the distal end surface of the insertion portion 11 in the insertion direction into the body cavity by operating the foot switch 6b.

Figure 2:
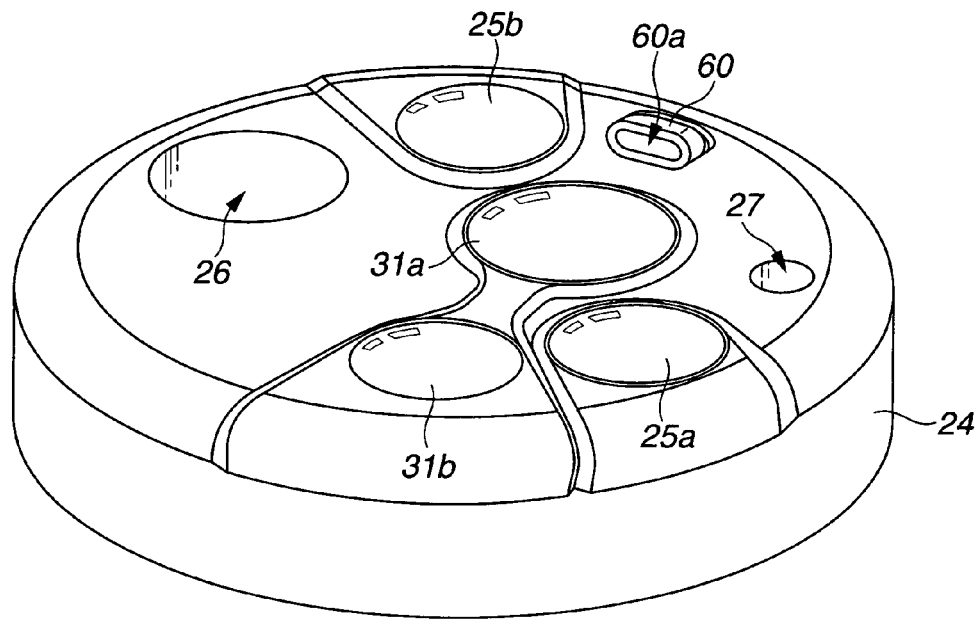
FIG. 2 is a perspective view showing a distal end cover of the endoscope of FIG. 1.
Figure 3:
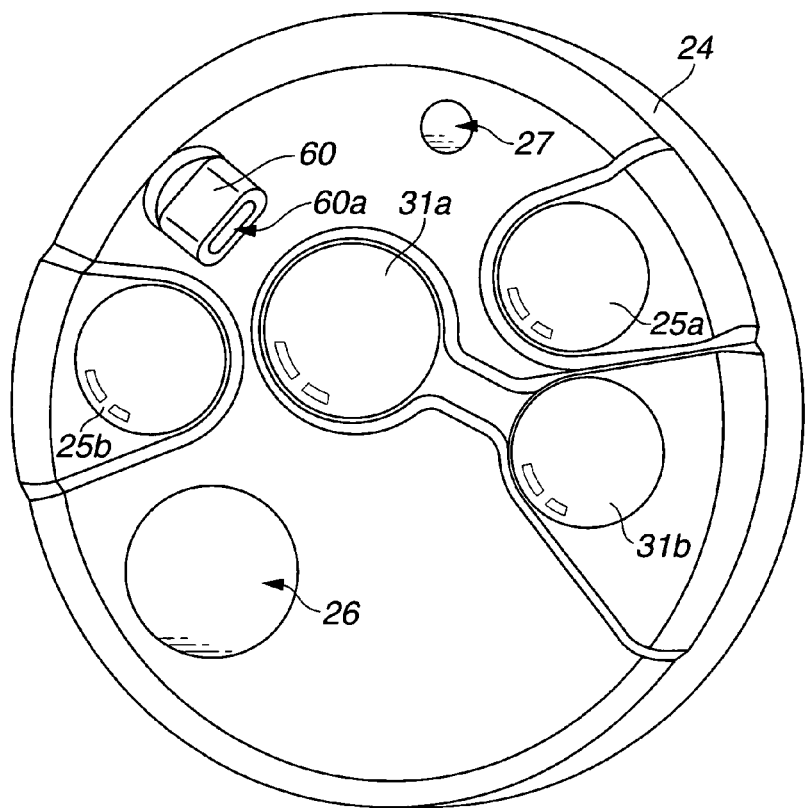
FIG. 3 is a perspective view, which is different from FIG. 2, showing the distal end cover of the endoscope of FIG. 1.
Figure 4:
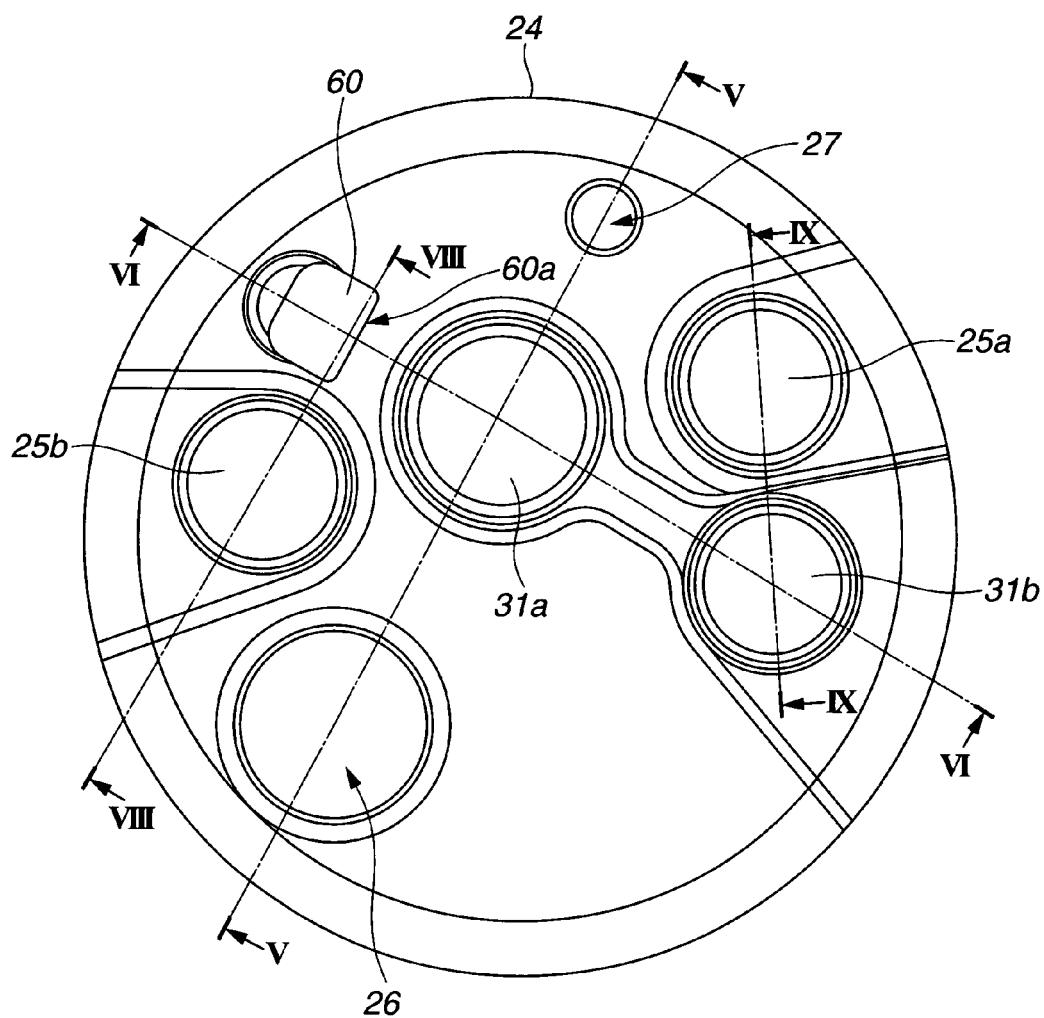
FIG. 4 is a plan view of the distal end cover of the endoscope of FIG. 1 viewed from the front.

As shown in FIGS. 2 to 4, to the distal end cover 24 provided on the distal end portion 15 of the insertion portion 11, provided are an observation lens 31a of the normal light image pickup unit 31A, an observation lens 31b of the fluorescent light image pickup unit 31B, two illumination lenses 25a, 25b as observation windows configuring a first illumination optical system and a second illumination optical system, an aperture portion 26 of the treatment instrument channel, and an aperture portion 27 of the forward water-feeding channel. In addition, on the distal end cover 24, the air/water feeding nozzle 60 is disposed such that a spouting port 60a faces the observation lenses 31a, 31b, as described above.

The observation lens 31a disposed on the distal end cover 24 of the distal end portion 15 condenses the light incident on the normal light image pickup unit 31A. Moreover, the observation lens 31b disposed on the distal end cover 24 of the distal end portion 15 condenses the light incident on the normal light image pickup unit 31B.

Note that, FIGS. 2 and 3 are perspective views showing the distal end cover part of the endoscope of FIG. 1. FIG. 4 is a plan view of the distal end cover of the endoscope of FIG. 1 viewed from the front. In addition, the two observation lenses 31a, 31b are the optical members.

To be concrete, the observation lens 31a as the observation window and an optical member configuring an image pickup portion for normal light observation is disposed at the approximately center of the distal end surface of the generally circular-shaped distal end cover 24 when viewed the distal end portion 15 from the distal end thereof, and the illumination lenses 25a, 25b are provided on the right and left when viewed facing the paper surface of FIG. 4, respectively, so as to sandwich the observation lens 31a. Furthermore, on the distal end surface of the distal end cover 24, provided are the aperture portion 27 of the forward water-feeding channel on the upper right side of the observation lens 31a facing the paper surface of FIG. 4, the air/water feeding nozzle 60 on the upper left side, the observation lens 31b as the observation window and the optical member configuring the image pickup portion for the special light observation on the lower right side and the aperture portion 26 of the treatment instrument channel on the lower left side, respectively.

Note that, detailed description will be made later on arrangements of the respective observation lenses 31a, 31b, provided on the distal end cover 24, the respective aperture portions 26, 27, and the air/water feeding nozzle 60 in the present embodiment.

Figure 5:
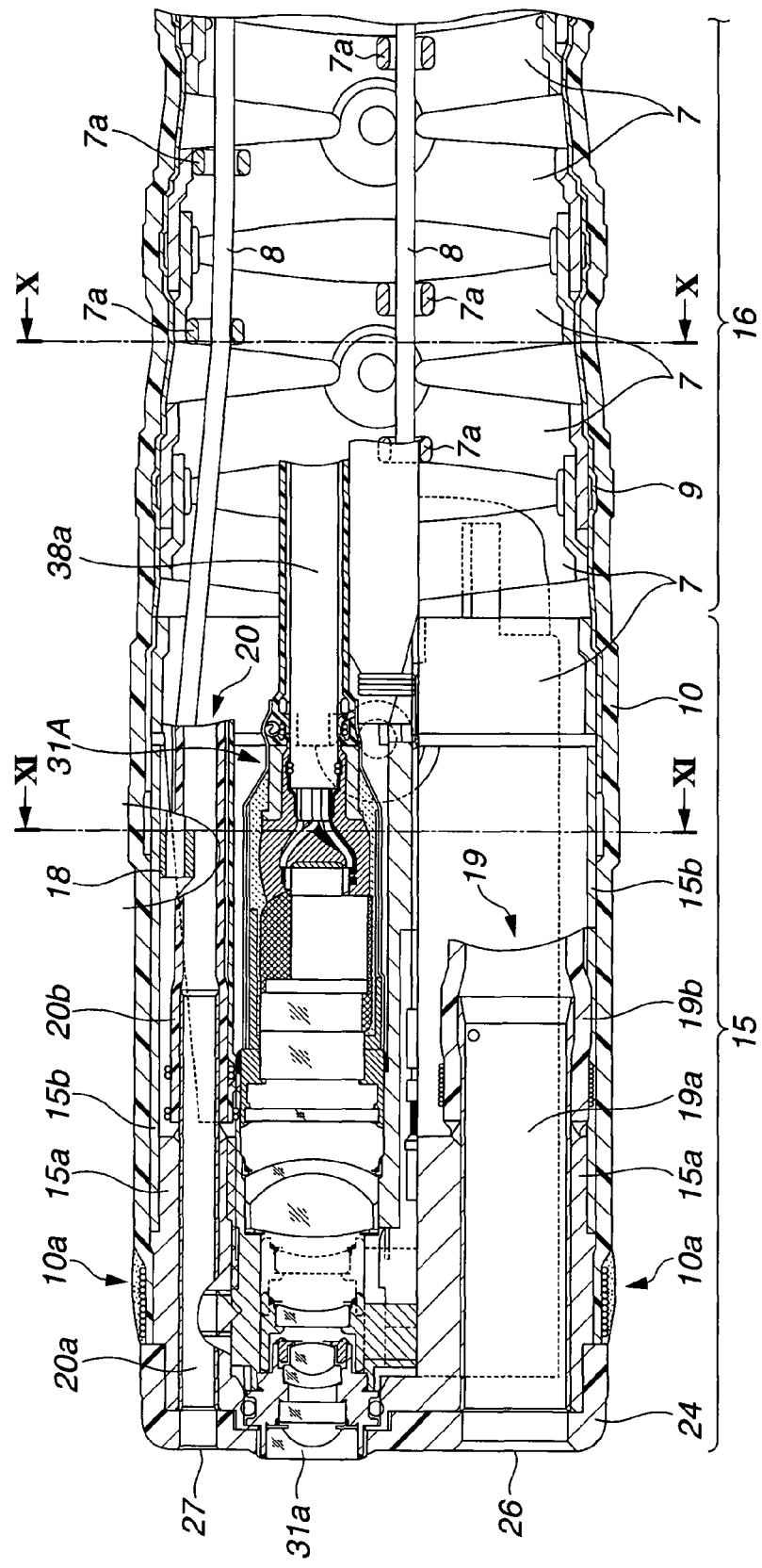
FIG. 5 is a cross-sectional view of a distal end portion and bending portion cut along V-V line of FIG. 4.
Figure 6:
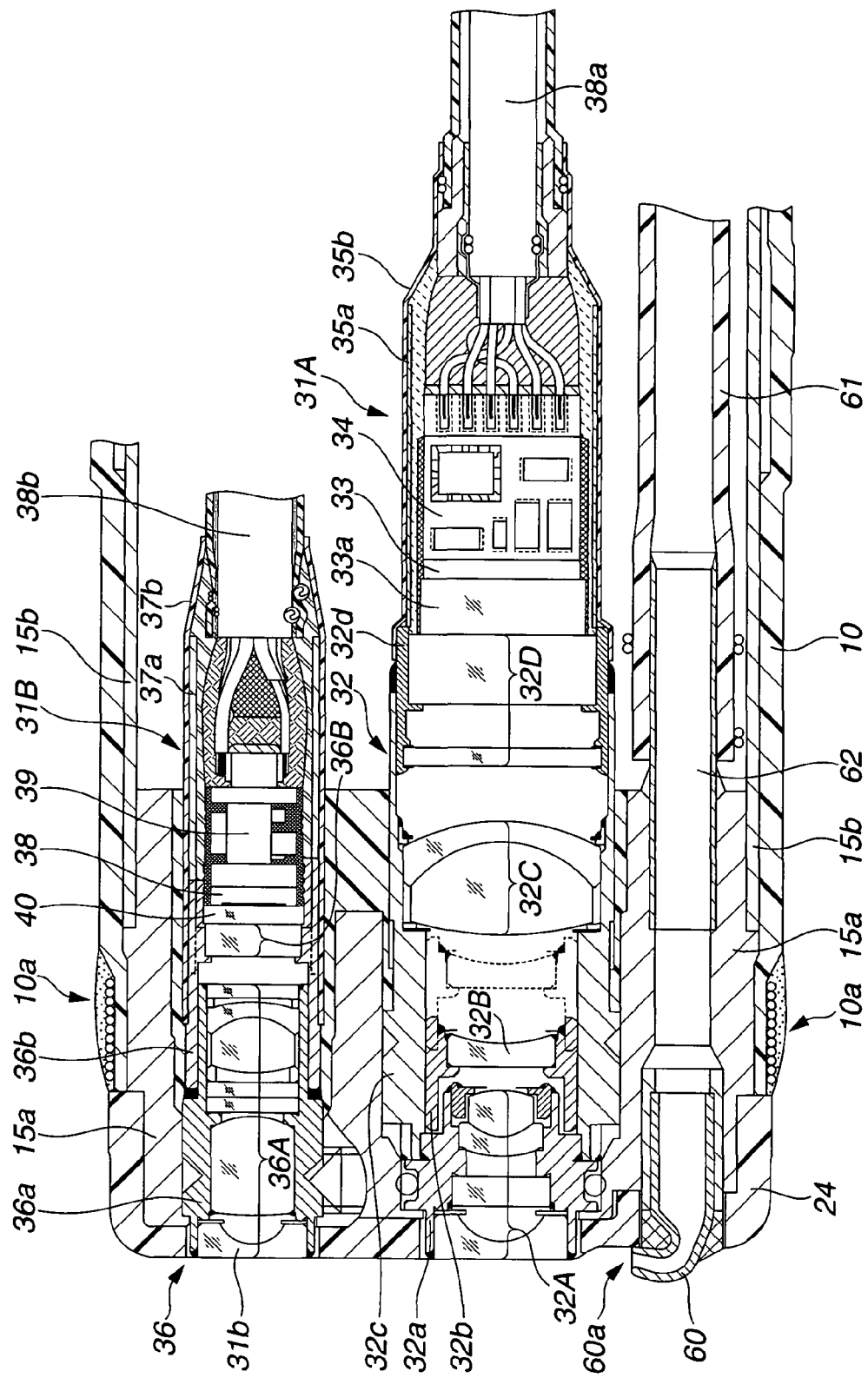
FIG. 6 is a cross-sectional view of the distal end portion cut along VI-VI line of FIG. 4.
Figure 7:
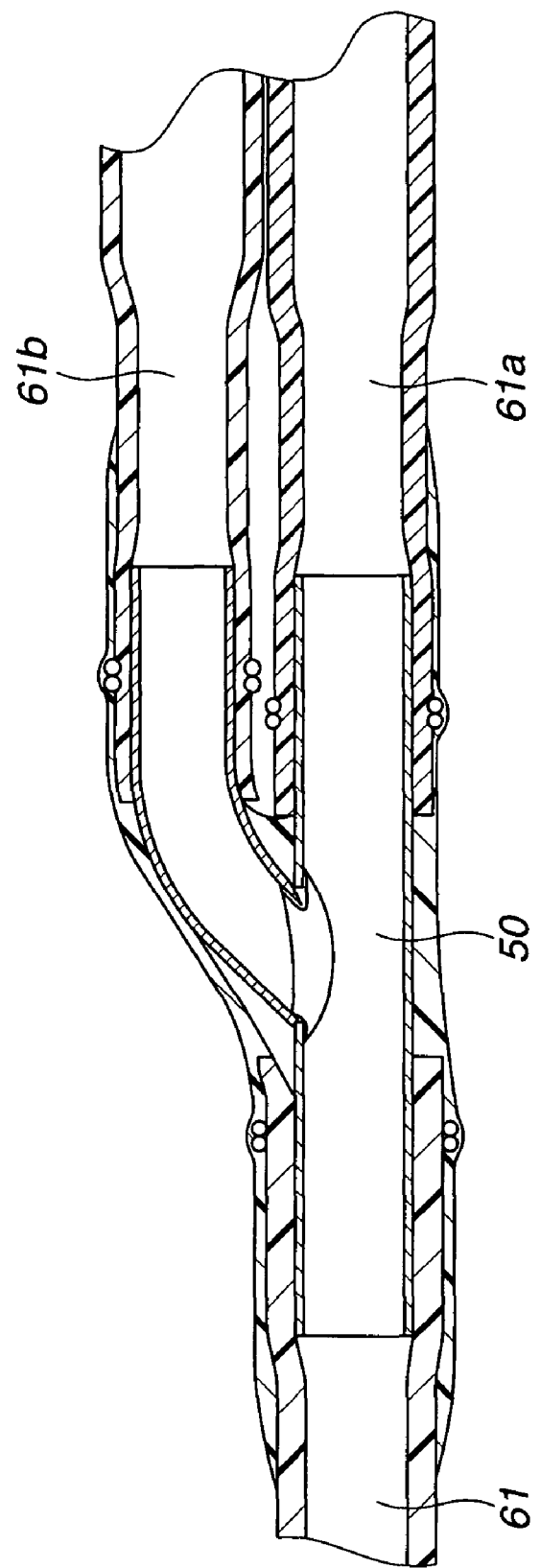
FIG. 7 is a cross-sectional view showing a diverging part of the air/water feeding duct of the endoscope of FIG. 1.
Figure 8:
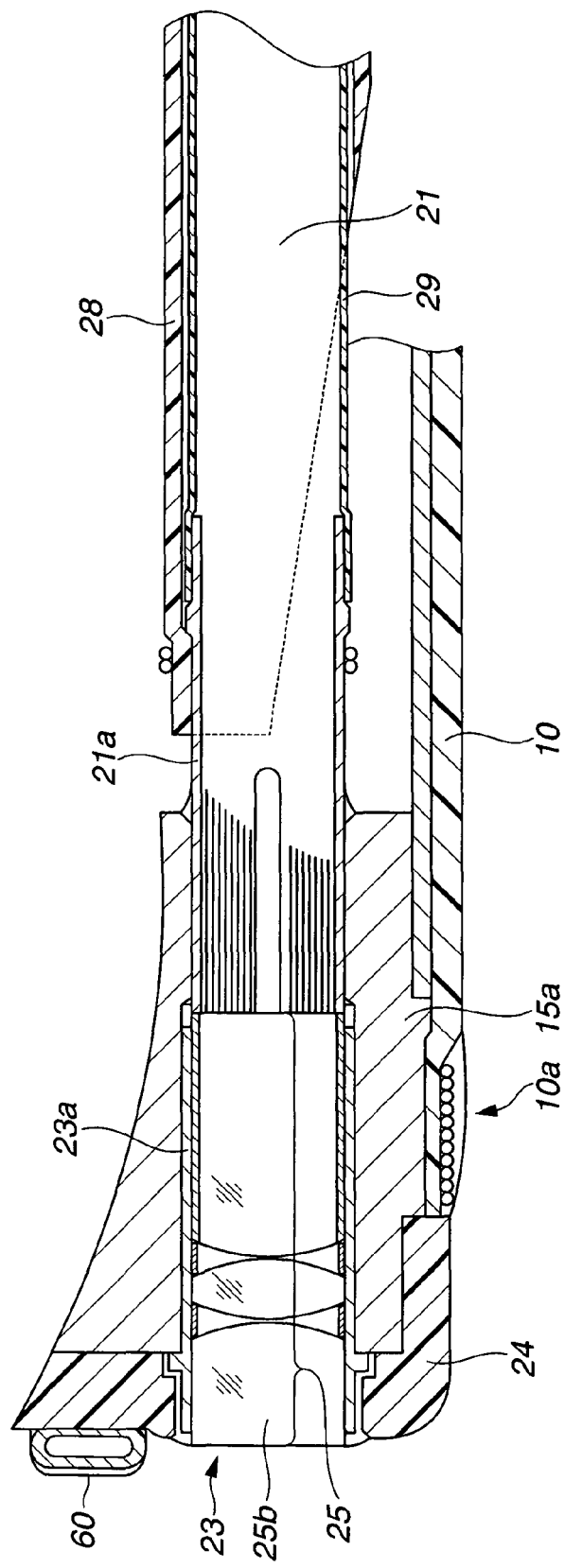
FIG. 8 is a cross-sectional view showing the distal end portion cut along VIII-VIII line of FIG. 4.
Figure 9:
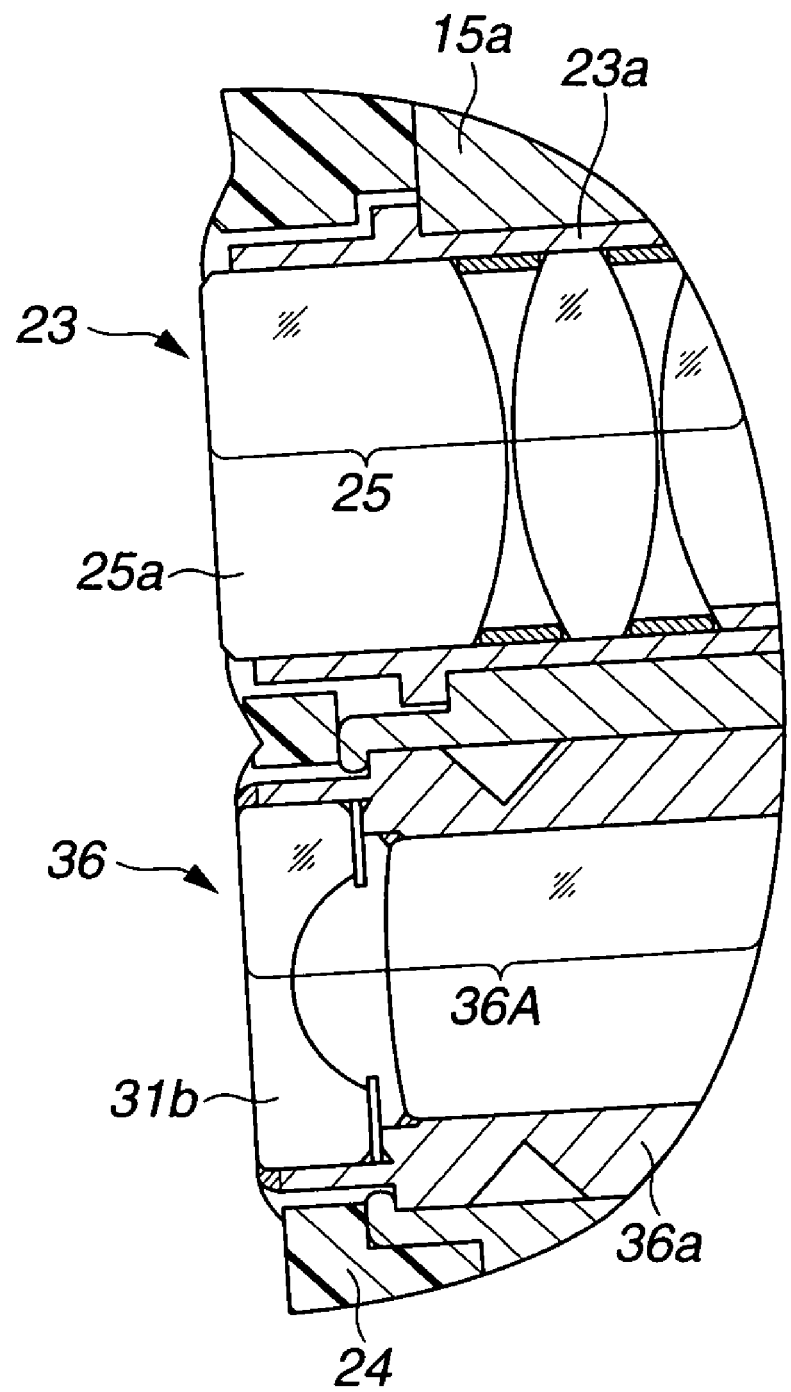
FIG. 9 is a cross-sectional view showing the distal end portion cut along IX-IX line of FIG. 4.
Figure 10:
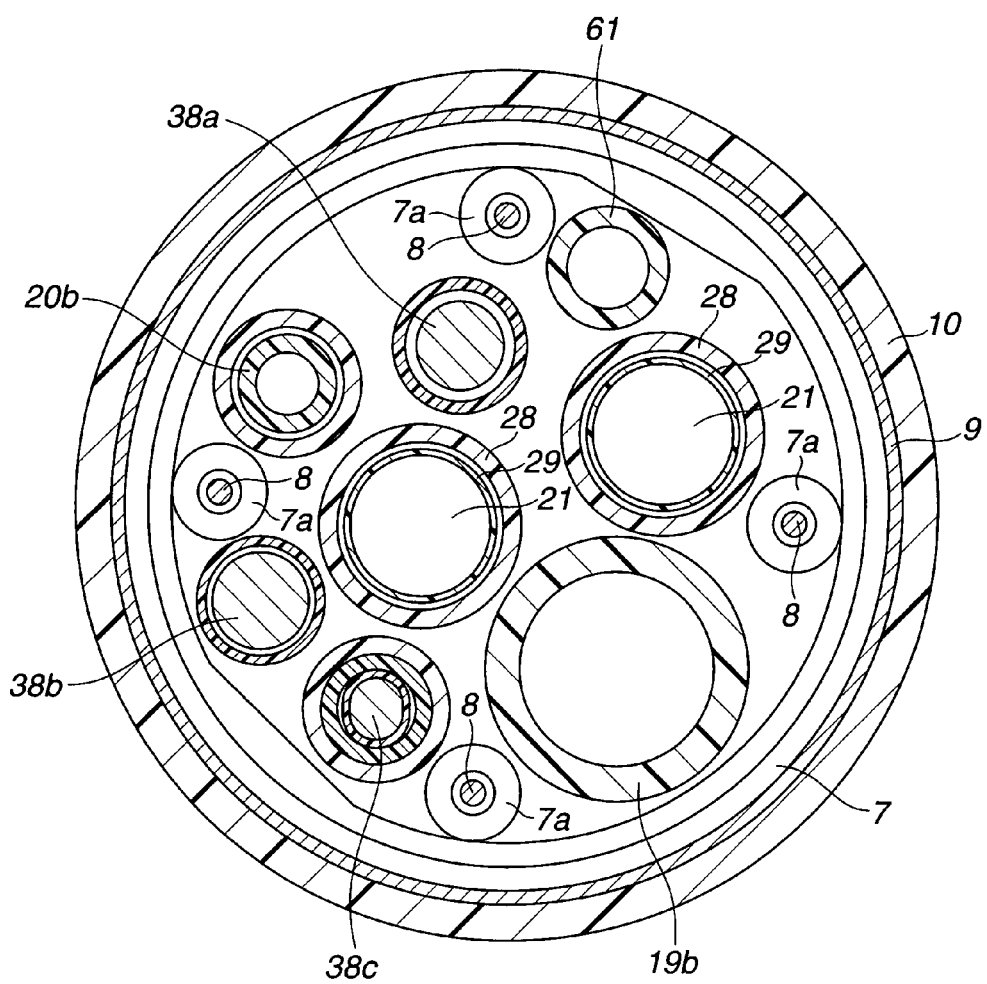
FIG. 10 is a cross-sectional view showing the distal end portion cut along X-X line of FIG. 5.
Figure 11:
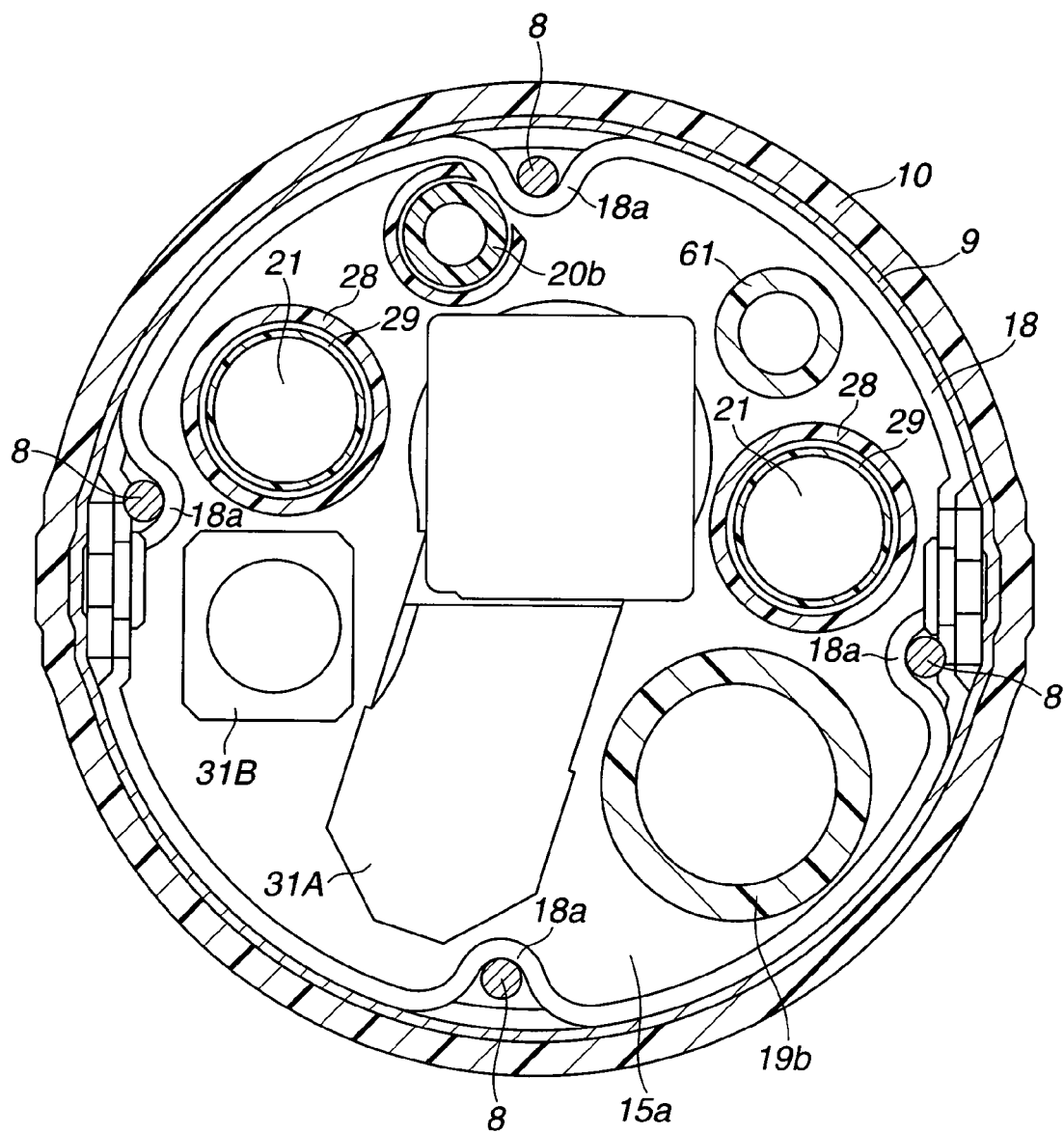
FIG. 11 is a cross-sectional view showing the bending portion cut along XI-XI line of FIG. 5.

Next, an internal configuration of the distal end part of the insertion portion 11 of the endoscope 2 according to the present embodiment will be described with reference to FIGS. 5 to 11. Note that FIG. 5 is a cross-sectional view of the distal end portion and the bending portion cut along V-V line of FIG. 4. FIG. 6 is a cross-sectional view of the distal end portion cut along VI-VI line of FIG. 4. FIG. 7 is a cross-sectional view showing a diverging part of the air/water feeding duct of the endoscope of FIG. 1. FIG. 8 is a partial cross-sectional view showing the distal end portion cut along VIII-VIII line of FIG. 4. FIG. 9 is a cross-sectional view showing the distal end portion cut along IX-IX line of FIG. 4. FIG. 10 is a cross-sectional view showing the distal end portion cut along X-X line of FIG. 5. FIG. 11 is a cross-sectional view showing the bending portion cut along XI-XI line of FIG. 5.

As shown in FIG. 5, the bending portion 16 of the endoscope 2 has a plurality of circular ring-shaped bending pieces 7 rotatably provided thereto in a linked manner.

The respective bending pieces 7 have four wire guards 7a fixed on inner circumferential surfaces thereof by means of adhesion. The four wire guards 7a are, as shown in FIG. 10, fixed on the inner circumferential surface of each of the bending pieces 7 at positions deviated from one another about the insertion axis by approximately 90 degrees.

Moreover, the plurality of bending pieces 7 are covered with a bending braid 9 formed by knitting thin wires in a pipe shape so as to cover the outer circumferences thereof, and moreover, on the bending braid 9, an outer covering is covered so as to keep watertightness. The bending portion 16 is formed by the bending pieces 7 having the above-described configuration, the bending braids 9, and the outer covering 10.

The outer covering 10 covers the bending portion 16 with one end of an outer circumferential part of the outer covering fastened to the distal end portion and the other end of an outer circumferential part fastened to the flexible tube portion 17.

In addition, the four bending operation wires 8 serving as bending operation means extending from the bending portion 16 toward the proximal end are inserted in the insertion portion 11. The four bending operation wires 8 have distal end parts which are held and fixed so as to be deviated from one another about the insertion axis by approximately 90 degrees by four fixing portions 18a (See FIG. 11. Note that only one of them is shown in FIG. 5) of a fixing ring 18 provided in the distal end portion 15, and configured such that the proximal ends thereof are each inserted into the wire guards 7a provided in each of the bending pieces 7.

Note that, the distal end portion 15 and the respective bending pieces 7 are joined such that the respective bending operation wires 8, which are held and fixed by the respective fixing portions 18a of the fixing ring 18 provided in the distal end portion 15 and inserted into the respective wire guards 7a of each of the bending pieces 7, are almost linearly disposed in a state where the insertion axis of the bending portion 16 is almost linear.

In addition, as shown in FIG. 1, the proximal end portions of the bending operation wires 8 are provided in the operation portion 12, and the bending operation wires 8 are connected to a bending operation mechanism not shown connected to a bending operation knob to be alternately pulled and relaxed.

Pulling and relaxing the respective four bending operation wires 8 by a predetermined operation of the bending operation knob cause the bending portion 16 to be operated and bent in four directions. Note that the above-described four directions are directions generally coincide with four directions of up, down, left, and right of the endoscope image picked up by the respective image pickup units 31A, 31B to be displayed on the monitor 5, as described later.

In addition, the two bending operation wires 8 serving as first bending operation means for operating the bending portion 16 in the up and down directions and the two bending operation wires 8 serving as second bending operation means for operating the bending portion 16 in the left and right directions make a pair, respectively. That is, the two bending operation wires 8 respectively inserted and held by the two wire guards 7a positioned in directions corresponding to the up and down directions in the bending pieces 7 in the bending portion 16 are the first bending operation means, and the two bending operation wires 8 respectively inserted and held by the two wire guards 7a positioned in directions corresponding to the left and right directions in the bending pieces 7 in the bending portion 16 are the second bending operation means.

In the distal end portion 15, provided are a columnar member 15a made of a rigid metal and including a plurality of, or seven hole portions in the present embodiment, and a circular ring-shaped reinforcing ring 15b externally fitted with the proximal end side outer circumferential part of the columnar member 15a. In addition, the fixing ring 18 having the four fixing portions 18a is fitted by insertion on an inner circumferential side of the reinforcing ring 15b of the distal end portion 15. Furthermore, the proximal end part of the reinforcing ring 15b is connected to the bending piece 7 located at the distal-most end.

The two hole portions among the seven hole portions formed of the columnar member 15a in the distal end portion 15 form distal end parts of the treatment instrument channel 19 and the forward water-feeding channel 20, and in the remaining five hole portions, disposed respectively are the normal light image pickup unit 31A, the fluorescent light image pickup unit 31B, and the air/water feeding nozzle 60 which are described above, and two illumination lens units to be described later.

Note that, one hole portion of the seven hole portions of the columnar member 15a is fixed, for example, by first observation-optical-system-fixing means such as a screw and adhesive, and configures first observation-optical-system-disposing means in which the normal light observation unit 31A including the observation lens 31a is disposed. In addition, another one hole portion is fixed, for example, by second observation-optical-system fixing means such as screw and adhesive, and configures second observation-optical-system-disposing means in which the fluorescent light observation unit 31B including the observation lens 31b is disposed. Moreover, in another two hole portions, two illumination lens units, which include illumination lenses 25 serving as the first and the second illumination optical systems, respectively, are each fixedly disposed by first and second illumination-optical-system-fixing means such as a screw and adhesive, for example. One of the two holes configures first illumination optical system-disposing means and the other configures second illumination-optical-system-disposing means.

Another hole portion among the seven hole portions, in which the air/water feeding nozzle 60 as the air/water feeding portion is disposed, configures air/water-feeding-portion-disposing means for fixedly disposing the air/water feeding nozzle 60 by first air/water-feeding portion-fixing means such as a screw and adhesive, for example. Furthermore, another hole portion among the seven hole portions in which the treatment instrument channel 19 as a first endoscope duct is disposed configures first endoscope-duct-disposing means, and yet another hole portion in which the forward water-feeding channel 20 as a second endoscope duct is disposed configures a second endoscope-duct-disposing means. Note that the treatment instrument channel 19 is fixedly disposed in one hole portion among the seven hole portions by first endoscope-duct-fixing means such as a screw and adhesive, for example, and the forward water-feeding channel 20 is fixedly disposed in another one hole portion by second endoscope-duct-fixing means such as a screw and adhesive, for example.

The treatment instrument channel 19 includes: the aperture portion 26 which opens on the distal end cover 24 provided on the distal end surface of the distal end portion 15, a generally cylindrical tube member 19a fitted by insertion in the hole portion of the columnar member 15a of the distal end portion 15, and a treatment instrument duct 19b formed of a flexible tube of which distal end part covers a proximal end part of the tube member 19a and connected and fixed thereto by a spool.

The treatment instrument duct 19b is inserted in the insertion portion 11, and of which proximal end is open at the operation portion 12, that is, open in the treatment instrument insertion port not shown in FIG. 1, as described above.

In addition, the forward water-feeding channel 20 similarly having the aperture portion 27 on the distal end cover 24 includes a generally cylindrical tube member 20a fitted by insertion in the hole portion of the columnar member 15a of the distal end portion 15, and a forward water-feeding duct 20b which covers a proximal end part of the tube member 20a and of which distal end part is connected and fixed by a spool.

The forward water-feeding duct 20b is inserted through the insertion portion 11, the operation portion 12 and the universal cable 13, to reach the connector 14, and is connected to the forward water-feeding device 6a. Note that, as described above, the forward water-feeding duct 20b as the forward water-feeding channel 20 includes the forward water-feeding button not shown placed in the operation portion 12.

As shown in FIG. 6, the air/water feeding nozzle 60 is a tubular member bent in an approximate L shape, and of which proximal end part is fitted by insertion in the hole portion of the columnar member 15a of the distal end portion 15 such that the distal end side spouting port 60a faces outer surface sides of the respective observation lenses 31a, 31b.

To a proximal end side of the hole portion of the columnar member 15a in which the air/water feeding nozzle 60 is disposed, a distal end part of the tube member 62 is fitted by insertion, and a proximal end part of the tube member 62 is connected to the air/water feeding duct 61. Note that the tube member 62 and the air/water feeding duct 61 are connected and fixed by a spool.

The air/water feeding duct 61 has, as shown in FIG. 7, a proximal end part connected to a diverging tube 50, and diverging end portions of the diverging tube 50 are connected to distal end parts of the air feeding duct 61a and the water feeding duct 61b, respectively. This allows the air/water feeding duct 61 to communicate with the air feeding duct 61a and the water feeding duct 61b. Note that the respective ducts 61, 61a, 61b are connected and fixed to the diverging tube 50 by the spool, and the respective connecting parts and around the entirety of the diverging tube 50 are applied with adhesive, for example, thereby allowing the respective connecting parts to be kept airtight (watertight).

In addition, into the two of the seven hole portions formed in the columnar member 15a of the distal end portion 15, illumination lens units 23 are fitted by insertion from a distal end side of the holes, respectively, and to proximal end parts of the holes, distal end parts of the light guides 21 are fitted by insertion, respectively. As shown in FIGS. 8 and 9, each of the illumination lens units 23 includes a plurality of illumination lenses 25, and a holding barrel 23a for holding the illumination lenses 25. Note that the two illumination lens units 23 in the present embodiment include the illumination lenses 25a, 25b which are the distal-most end lenses among the illumination lenses, respectively.

The light guide 21 of which distal end part is covered with a cylindrical member 21a is coated by an outer covering 29 binding up a plurality of fibers. A proximal end part of the cylindrical member 21a is connected and fixed to a tube 28 of which distal end part is spool-fixed, and into the tube 28, the light guide 21 coated by the outer covering 29 is inserted.

Returning to FIG. 6, the normal light image pickup unit 31A includes a lens unit 32, and image pickup device 33 which is a CCD or a CMOS and the like, and a circuit substrate 34.

The lens unit 32 includes first to fourth lens groups 32A to 32D, and first to fourth lens barrels 32a to 32d. In the present embodiment, the first lens group 32A formed by four objective lenses including the observation lens 31a, the second lens 32B formed by one objective lens, the third lens group 32C formed by two objective lenses, and the fourth lens group 32D formed by three objective lenses are held by the first lens barrel 32a, the second lens barrel 32b, the third lens barrel 32c, and fourth lens barrel 32d, respectively.

In addition, the second lens barrel 32b holding the second lens 32B is a moving barrel advanceable and retractable for zooming with respect to a photographing optical axis direction. Note that, when the user operates zooming operation lever, not shown, provided in the operation portion 12, the second lens barrel 32b is advanced or retracted with respect to the photographing optical axis direction by driving means such as a motor or actuator, not shown, provided in the normal light image pickup unit 31A, for example. With such a configuration of the endoscope 2, the normal light image pickup unit 31A is capable of displaying a part of the endoscope image obtained in a field of view of the observation lens 31a in an enlarged manner on the monitor 5, for example.

Note that, the driving means for advancing and retreating the second lens barrel 32b with respect to the photographing optical axis is supplied with a drive-stop signal by the signal line 38c shown in FIG. 10. The signal line 38c is inserted from the normal light image pickup unit 31A, through inside of the insertion portion 11, to the operation portion 12.

The image pickup device 33 includes on a light receiving surface side a cover lens 33a which is juxtaposed on a proximal end side of the objective lens positioned at the proximal-most end of the fourth lens barrel 32d, and outputs to a circuit substrate 34 an electrical signal corresponding to an optical image. The circuit substrate 34 has electrical parts and a wiring pattern, and photoelectrically converts the optical image from the image pickup device 33 into an electrical image signal to output the image signal to the signal cable 38a. Note that, to the circuit substrate 34, a plurality of signal lines of the signal cable 38a are connected by means of soldering and the like.

The cover lens 33a, the image pickup device 33, the circuit substrate 34 and the distal end part of the signal cable 38a respectively have outer circumferential portions which are integrally covered with, for example, an insulation sealing resin and coated with a reinforcing circular ring portion 35a and an insulating tube 35b.

In addition, the signal cable 38a transmits the image signal obtained from the image pickup device 33 of the normal light image pickup unit 31A and the circuit substrate 34 to the signal processing circuit 46 of the processor 4, via the relay substrate 42 of the connector 14 and the signal cable 43 which are shown in FIG. 1.

On the other hand, the fluorescent light image pickup unit 31B includes, similarly as the normal light image pickup unit 31A, the lens unit 36, an image pickup device 38 such as a CCD or a CMOS and the like, and a circuit substrate 39.

The lens unit 36 includes first and second lens groups 36A, 36B, and first and second lens barrels 32a, 32b. In the present embodiment, the first lens group 36A formed of seven objective lenses including the observation lens 31b and the second lens 36B are held by the first lens barrel 36a and the second lens barrel 36b, respectively.

The image pickup device 38 includes on a light receiving surface side a cover lens 40 which is juxtaposed on a proximal end side of the objective lens positioned at the proximal-most end of the second lens barrel 36b and outputs to the circuit substrate 39 an electrical signal corresponding to an optical image. The circuit substrate 39 has electrical parts and a wiring pattern similarly as the circuit substrate 34 of the normal light image pickup unit 31A, and to the circuit substrate 39, a plurality of signal lines included in the signal cable 38a are connected by means of soldering and the like. In addition, the circuit substrate 39 photoelectrically converts the optical image from the image pickup device 38 into an electrical image signal to output the image signal to the signal cable 38b.

The cover lens 40, the image pickup device 33, the circuit substrate 34 and the distal end part of the signal cable 38a respectively have outer circumferential portions which are integrally covered with, for example, an insulation sealing resin and coated with a reinforcing circular ring portion 35a and an insulating tube 35b.

In addition, the signal cable 38b transmits the image signal obtained from the image pickup device 38 and the circuit substrate 39 of the fluorescent light image pickup unit 31B to the signal processing circuit 46 of the processor 4, via the relay substrate 42 and the signal cable 43 of the connector 14 which are shown in FIG. 1.

The normal light image pickup unit 31A and the fluorescent light image pickup unit 31B described above are fitted by insertion into predetermined hole portions provided in the columnar member 15a of the distal end portion 15, respectively, and firmly fixed with fixing members such as screws along with adhesive and the like.

Furthermore, in the present embodiment, the observation lens 31a disposed at the distal end of the normal light image pickup unit 31A has a larger lens diameter (diameter as outer diameter) compared with the observation lens 31b disposed at the distal end of the fluorescent light image pickup unit 31B.

The disposition directions of the respective image pickup units 31A, 31B in the distal end portion 15 are determined such that the respective light receiving surfaces of the two image pickup devices 33, 38 are orthogonal with respect to the insertion axis of the insertion portion 11, and a horizontal transfer direction and a vertical transfer direction, as charge transfer directions, of the image pickup device 33 coincide with a horizontal transfer direction and a vertical transfer direction as the charge transfer directions of the image pickup device 38, respectively.

Subject images photographed by the respective image pickup units 31A, 31B are displayed on the monitor 5, and the up/down direction and left/right direction of the monitor 5 coincide with the vertical transfer directions and the horizontal transfer directions of the CCD elements and the CMOS elements of the respective image pickup devices 33, 38, respectively. That is, the up, down, left, and right directions of the endoscope images photographed by the respective image pickup units 31A, 31B coincide with the up, down, left, and right directions of the monitor 5.

The up, down, left, and right directions of the bending portion 16 of the insertion portion 11 are determined so as to correspond to the up, down, left, and right directions of the endoscope image displayed on the monitor 5. Accordingly, the four bending operation wires 8 inserted in the bending portion 16 are pulled and relaxed by predetermined operations of the bending operation knob provided in the operation portion 12, as described above, thereby allowing the bending portion 16 to be bendable in four directions, that is, the up, down, left, and right directions corresponding to the up, down, left, and right directions of the endoscope image displayed on the monitor 5.

That is, in the respective image pickup units 31A, 31B, even if the normal light observation and the fluorescent light observation are switched each other, the up, down, left, and right directions of the endoscope image displayed on the monitor 5 always coincide with those of the bending operation directions of the bending portion 16, and the disposition directions of the image pickup units 31A, 31B in the distal end portion 15 are determined such that the horizontal transfer direction and the vertical transfer direction of the image pickup device 33 coincide with the horizontal transfer direction and the vertical direction of the image pickup device 38, respectively.

With such a configuration, the user can perform a bending operation of the bending portion 16 in up, down, left, and right directions without feeling a sense of discomfort with respect to the up, down, left, and right directions of the endoscope image displayed on the monitor 5 when the endoscope image is switched between the normal light observation image and the fluorescent light observation image.

Note that, in the following description, the up/down direction as a first direction will be described as the direction approximately coincident with the up/down direction of the endoscope image displayed on the monitor 5 and the up/down direction in which the bending portion 16 is operated and bent. In addition, the monitor 5 is generally disposed such that the up/down direction thereof approximately coincides with the plumb up/down direction. Furthermore, the left/right direction as a second direction approximately orthogonal to the above-described up/down direction will be described as a direction approximately coincident with the left/right direction of the endoscope image displayed on the monitor 5 and the left/right direction in which the bending portion 16 is operated and bent.

Here, the action of the above-described endoscope system 1 will be described.

As shown in FIG. 1, the user connects the connector 14 of the endoscope 2 to the light source device 3, then connects one end and the other end of the scope cable 44 with the connector 14 and the processor 4, respectively. In addition, the user connects the air feeding duct 61a and the water feeding duct 61b to the air/water feeding device 6.

Then, the user turns on power switches of the light source device 3 and the like to set the device and the like in an operation state, respectively. At this time, the control circuits 47, 58 of the processor 4 and the light source device 3 become a state in which they can transmit and receive a control signal and the like.

Furthermore, in a state immediately after the activation, the relay substrate 42 is set such that the normal light image pickup unit 31A is selected. Moreover, the control circuit 47 performs a control operation to set the normal light observation state. That is, the control circuit 47 transmits a control signal to the control circuit 58 of the light source device 3 to set the light source device 3 in a state where illumination light for normal light observation is supplied.

In addition, the control circuit 47 controls to drive the CCD driving circuit 45a, and sets the operation state of the signal processing circuit 46 in the normal light observation mode.

The user inserts the insertion portion 11 of the endoscope 2 into a body cavity to set such that a diseased part and the like as a subject to be diagnosed can be observed.

The light source device 3 becomes the state where the illumination light for normal light observation is supplied, as described above. In this state, the rotation filter 53 is rotated and driven by the motor 55 in a state where the RGB filter are disposed in the illumination optical path. Then red, green, and blue illumination lights are supplied to the light guide 21 as frame sequential lights. Synchronizing with this, the CCD driving circuit 45a outputs a CCD driving signal, and the illumination lights illuminate the diseased part in a patient's body cavity via the illumination lenses 25a, 25b.

The images of the illuminated subject such as the diseased part pass through the lens unit 32 of the normal light image pickup unit 31A to be formed on the light receiving surface of the image pickup device 33, and then photoelectrically converted. Then, the image pickup device 33 outputs the signals obtained by the photoelectric conversion, in response to application of a driving signal. The outputted signals are inputted to the signal processing circuit 46 through the signal cable 38a and the common signal cable 43 selected by the relay substrate 42.

The signals inputted to the signal processing circuit 46 are A/D converted in the circuit to be temporarily stored in an RGB memory.

After that, the signals stored in the RGB memory are simultaneously read out to be synchronized R, G, B signals, and then D/A converted to be analog R, G, B signals, thereafter being color-displayed on the monitor 5.

Then, when the user desires to further inspect the diseased part which has been observed by normal light observation by performing the fluorescent light observation, the user turns on the control switch 48a. Then, the control circuit 47 performs switching control of the relay substrate 42 in response to the switch instruction signal outputted from the control switch 48a, and sets the light source device 3 in a state where excitation light for fluorescent light observation is supplied via the control circuit 58.

In addition, the control circuit 47 controls the driving circuit 45b in an operation state and sets the signal processing circuit 46 in a processing mode by the fluorescent light observation.

In this case, the control circuit 58 in the light source device 3 moves the rotation filter 53 as well as the motor 55 in a direction orthogonal to the illumination optical path by means of the gear-equipped motor 57 such that an excitation light filter is disposed on the illumination optical path.

In this state, light from the lamp 51 is supplied to the light guide 21 as the excitation light having a wavelength band around 400 to 450 nm, for example, by passing through the excitation light filter. Then, the excitation light is illuminated onto the diseased part or the like in the body cavity via the illumination lenses 25a, 25b.

If the diseased part or the like on which the excitation light is illuminated is a cancer tissue, they absorb the excitation light to emit stronger fluorescent light, compared with the case where the disease part or the like is a normal tissue. The light from the part emitting the fluorescent light passes through the lens unit 36 of the fluorescent light image pickup unit 31B and image-formed on the light receiving surface of the image pickup device 38 to be photoelectrically converted.

Then the image pickup device 38 outputs the signals obtained by the photoelectric conversion and amplification in response to application of a driving signal from the driving circuit 45b. The signals obtained by the photoelectric conversion and the amplification are inputted to the signal processing circuit 46 via the signal cable 38b and the common signal cable 43 selected by the relay substrate 42.

The signals inputted in the signal processing circuit 46 are A/D converted in the circuit and simultaneously stored in the RGB memory, for example.

The signals stored in the RGB memory is simultaneously read out to be synchronized R, G, B signals, and then D/A converted into analog R, G, B signals, thereafter being monochrome-displayed on the monitor 5.

Note that signals inputted in the signal processing circuit 46 may be turned into pseudo-colors to be displayed by comparing the levels of the signals with a plurality of threshold values and changing colors to be allocated to the signals depending on the comparison result.

Thus, with the present embodiment, in addition to the normal light observation, the fluorescent light observation can be performed, thereby realizing the endoscope facilitating a diagnosis compared with the endoscope capable of performing only the normal light observation. Also, with the present embodiment, the image pickup units 31A, 31B are respectively provided, so that it is possible to obtain the special light observation image as a first observation image, that is, the fluorescent light observation image, and the normal light observation image as a second observation image. That is, the image pickup unit 31B as the first image pickup portion can obtain the special light observation image as the first observation image based on the light condensed by the observation lens 31b disposed on the distal end cover 24 of the distal end portion 15. In addition, the image pickup unit 31A as the second image pickup portion can obtain the normal light observation image as the second observation image based on the light condensed by the observation lens 31a disposed on the distal end cover 24 of the distal end portion 15.

In a case of performing the fluorescent light observation, in particular, the images based on weaker light are often picked up compared with the case of normal observation. Therefore, it is desirable to employ an image pickup device having a high S/N (signal to noise) ratio in the fluorescent light observation. In a case where the image pickup for normal observation is used also as the one for fluorescent light observation, the picked-up image tends to have a low S/N ratio. However, in the present embodiment, the image pickup device 38 dedicated and suitable for the fluorescent light observation is employed, thereby allowing the fluorescent light image with high S/N ratio to be obtained.

Also, the switching relay substrate 42 is provided, thereby allowing a configuration in which only one of the two image pickup units 31A, 31B is connected to the processor 4, so that the endoscope system 1 can be formed to have a compact configuration compared with the one in which it is necessary to constantly drive the two image pickup units 31A, 31B, and perform signal processing with respect to the units.

Furthermore, in the present embodiment, one air/water feeding nozzle 60 is employed to keep the both observation lenses 31a, 31b clean by spraying gas or water on the outer surfaces of the lenses, thereby ensuring the excellent observation field of view. As a result, the insertion portion 11 have a smaller diameter, thereby reducing pain imposed on a patient when a user inserts the insertion portion into the patient's body cavity and also expanding regions in body cavities where the endoscope is insertable.

In addition, the endoscope 2 according to the present invention has the same external configuration as an existing endoscope including only the image pickup unit for normal light observation, and can be used also as the endoscope for normal light observation similarly as the existing endoscope, by connecting, via the scope cable 44, to a processor, not shown, for driving and performing signal processing with respect to the existing endoscope including only the image pickup unit for normal light observation. That is, the endoscope 2 can be also used by connecting with the existing processor, while keeping a similar compatibility with the existing endoscope including only the image pickup unit for normal light observation.

The endoscope 2 according to the present invention has various characteristics (effects) with structure described below.

First, detailed description will be made on disposition of the air/water feeding nozzle 60, and the respective observation lenses 31a, 31b which are provided on the distal end cover 24, with reference to FIG. 12.

Figure 12:
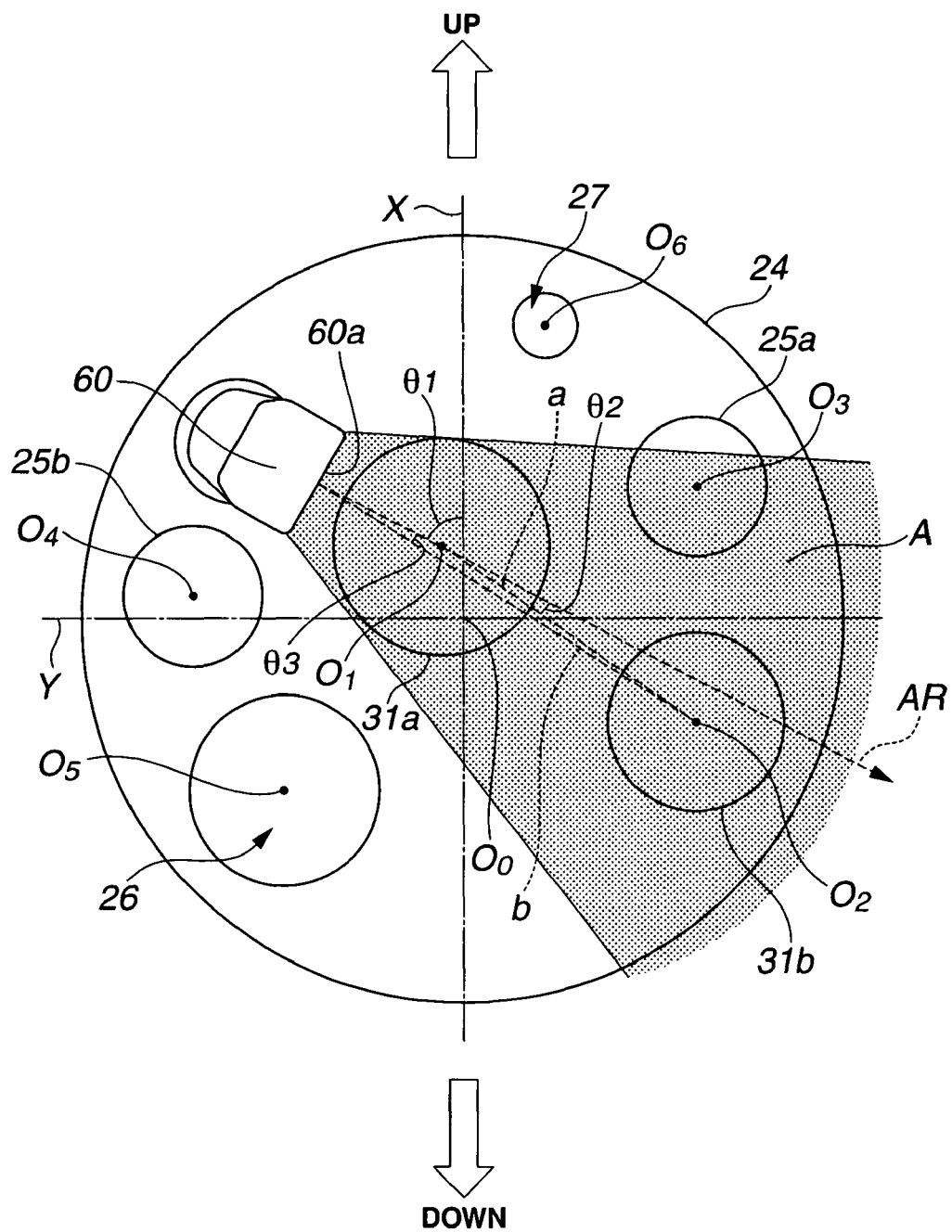
FIG. 12 is a plan view, which is different from FIG. 4, showing the distal end cover of the endoscope in FIG. 1 viewed from the front.

FIG. 12 is a front view showing the distal end surface of the distal end cover.

Note that, in the description below, the centers of the distal end cover 24, the observation lens 31a of the normal light image pickup unit 31A, and the observation lens 31b of the fluorescent light image pickup unit 31B are referred to as $O_0$, $O_1$, and $O_2$, respectively. In addition, a center of the illumination lens 25a as a first center to be described later and a center of the illumination lens 25b as a second center are referred to as $O_3$ and $O_4$, respectively. A center of the aperture portion 16 of the treatment instrument channel 19 and a center of the aperture portion 27 of the forward water-feeding channel 20 are referred to as $O_5$ and $O_6$, respectively. Furthermore, a line passing through the center $O_0$ of the distal end surface of the distal end cover 24 in the up/down bending direction of the bending portion 16 and a line in the left/right bending direction of the bending portion 16 are defined as a vertical line X and a horizontal line Y, respectively. Note that, the vertical line X in the present embodiment is equal to the plumb line in the following description.

As described above, the air/water feeding nozzle 60 is provided on the upper left side of the distal end surface of the distal end cover 24 when viewed facing the paper surface of FIG. 12 such that the spouting port 60a faces toward the observation lens 31a. Note that the air/water feeding nozzle 60 may be provided on the upper right side of the distal end surface of the distal end cover 24 when viewed facing the paper surface of FIG. 12 such that the spouting port 60a faces toward the observation lens 31a. At this time, the air/water feeding nozzle 60 and the respective observation lenses 31a, 31b are so disposed as to be almost linearly juxtaposed on the distal end surface of the distal end cover 24.

In the present embodiment, the air/water feeding nozzle 60 is provided on the distal end surface of the distal end cover 24 such that the gas or liquid such as air or distilled water spouted from the spouting port 60a of the air/water feeding nozzle 60 is spouted in the arrow line AR direction in the drawing. The air/water feeding nozzle 60 spouts to diffuse the gas or liquid such as air or distilled water from the spouting port 60a into a gas/liquid spouting range A. Note that the arrow line AR is a line in a direction approximately orthogonal to the distal end surface of the air/water feeding nozzle 60 having the spouting port 60a and passing through the center of the hole surface of the spouting port 60a.

The disposition direction of the air/water feeding nozzle 60 about an axis, that is, a direction in which the spouting port 60a faces, is determined such that the observation optical axis passing the center $O_1$ of the observation lens 31a intersects the arrow line AR described above. In other words, the direction in which the spouting port 60a of the air/water feeding nozzle 60 faces is determined such that the arrow line AR which is the spouting direction of the gas or liquid such as air or distilled water has a predetermined angle θ1 as a first angle with respect to the vertical line X.

Meanwhile, the observation lens 31b of the fluorescent light image pickup unit 31B is provided on the lower right side of the distal end surface of the distal end cover 24 facing the paper surface of FIG. 10 such that the outer surface of the observation lens 31b has at least a part intersecting the arrow line AR when viewing the distal end cover 24 from the distal end side thereof. In addition, the observation lens 31b is provided on the distal end surface of the distal end cover 24 such that the center $O_2$ thereof is positioned on the lower side than a segment of the arrow line AR.

As described above, the air/water feeding nozzle 60 and two observation lenses 31a, 31b are almost linearly juxtaposed on the distal end surface of the distal end cover 24.

In detail, a line a connecting the center $O_1$ of the observation lens 31a of the normal light image pickup unit 31A and the center $O_2$ of the observation lens 31b of the fluorescent light image pickup unit 31B is slightly deviated to the lower side by a predetermined angle θ2 with respect to the arrow line AR, when viewed from the distal end cover 24 from the distal end surface side thereof. In other words, a line b connecting the hole surface center of the spouting port 60a of the air/water feeding nozzle 60 and the center $O_2$ of the observation lens 31b is slightly deviated to the lower side by a predetermined angle θ3 with respect to the arrow line AR, when viewed from the distal end cover 24 from the distal end surface side thereof.

This allows the respective disposing positions of the observation lenses 31a, 31b on the distal end cover 24 to be determined, and in accordance with the positions, the direction of the spouting port 60a (the arrow line AR direction) of the air/water feeding nozzle 60 is determined. Moreover, the angles θ2, θ3 are set within a range such that the whole outer surface of the observation lens 31b is located within the gas/liquid spouting range A of the air/water feeding nozzle 60.

Note that the gas/liquid spouting range A of the air/water feeding nozzle 60 is set so as to contain the whole outer surface of the observation lens 31a of the normal light image pickup unit 31A, when viewed from the distal end side of the distal end cover 24.

In addition, the observation lens 31a having a larger lens diameter (diameter as the outer diameter) than the outer diameter of the observation lens 31b is provided on the distal end surface of the distal end cover 24 so as to be close to the air/water feeding nozzle 60.

That is, the distal end cover 24 has the air/water feeding nozzle 60 at a position on an upper side than the horizontal line Y approximately bisecting the bending up/down direction of the bending portion 16 with respect to a direction viewed from the distal end surface side, that is, up/down direction of the vertical transfer direction in which the image pickup devices 33, 38 included in the respective image pickup units 31A, 31B perform processings. In other words, the air/water feeding nozzle 60 is provided to the distal end cover 24 away from the horizontal line Y in a direction opposite to the spouting direction (arrow line AR direction).

Furthermore, the distal end cover 24 has the air/water feeding nozzle 60 provided such that a cross section of the air/water feeding nozzle 60 in a direction orthogonal to the longitudinal axis (axis parallel with the insertion direction) thereof is not positioned on the vertical line X which bisects a left/right direction (which is reverse to the bending left/right direction of the bending portion 16) with respect to the direction viewed from the distal end surface side of the distal end cover, that is, the left/right direction of the vertical transfer direction in which the image pickup devices 33, 38 included in the respective image pickup units 31A, 31B perform processings.

Note that, in the present embodiment, the air/water feeding nozzle 60 and the spouting port 60a are provided at a position on the distal end surface of the distal end cover 24 so as to be separated by a predetermined distance in the left direction from the vertical line X, when viewed from the distal end surface side of the distal end cover 24. That is, the air/water feeding nozzle 60 is disposed such that a longitudinal axis thereof is located at a position deviated to the upper side than the horizontal line Y bisecting the distal end cover 24 into upper and lower parts, and deviated to the left side from the vertical line X bisecting the distal end cover 24 into left and right parts, when viewed from the distal end surface side of the distal end cover 24.

As described above, the endoscope 2 of the present embodiment includes, on the distal end surface of the distal end cover 24, the air/water feeding nozzle 60, the observation lens 31a of the normal light image pickup unit 31A, and the observation lens 31b of the fluorescent light image pickup unit 31B which are almost linearly disposed. As a result, the endoscope 2 of the present embodiment is configured such that gas or water is sprayed from one air/water feeding nozzle 60 onto the outer surfaces of the respective observation lenses 31a, 31b to set the lenses in a clean state, thereby ensuring an excellent observation field of view.

In addition, the air/water feeding nozzle 60 is disposed such that the longitudinal axis thereof is located on the upper side than the horizontal line Y bisecting the distal end cover 24 into upper and lower parts, and at a position deviated by a predetermined distance from the vertical line X bisecting the distal end cover 24 into left and right parts. Therefore, when the insertion portion 11 is in an almost straight state, the air/water feeding duct 61 communicating with the air/water feeding nozzle 60 is inserted almost straight into the distal end portion 15 and the bending portion 16, without contacting the four fixing portions 18a of the fixing ring 18 provided in the distal end portion 15 and the four wire guards 7a provided respectively to each of the bending pieces 7 provided in the bending portion 16.

Moreover, disposition of the above-described air/water feeding nozzle 60 prevents the air/water feeding duct 61 from contacting the four bending operation wires 8 respectively held by insertion into the four wire guards of each of the bending pieces 7 in the bending portion 16. Therefore, in the endoscope 2 according to the present embodiment, movement of the bending operation wires 8 due to pulling and relaxing is not obstructed and the degradation of the bending operation wires 8 due to scratch can be prevented.

As a result, in the endoscope 2 according to the present embodiment, the insertion portion 11, particularly, the distal end portion 15 and the bending portion 16 have smaller diameter, thereby reducing the pain imposed on the patient at the time of insertion and expanding regions of body cavities where the endoscope is insertable.

In addition, the endoscope 2 is generally used by a user such that the up/down bending direction of the bending portion 16 coincides with the up and down in the plumb direction. Accordingly, the liquid such as distilled water spouted from the spouting port 60a of the air/water feeding nozzle 60 flows down to the lower side due to influence of gravitational force, on a far side from the spouting port 60a.

Furthermore, when the gas or liquid such as air or distilled water is spouted from the spouting port 60a of the air/water feeding nozzle 60 and also suction is performed through the treatment instrument channel 19, the gas or the water is subject to a pulling force in the direction of the aperture portion 26 due to a suction force from the aperture portion 26 of the treatment instrument channel 19 provided on the lower side of the distal end cover 24, resulting in a change of the flow direction of the gas or the air to the down bending direction side.

In view of such a circumstance, in the endoscope 2 of the present embodiment, on the distal end surface of the distal end cover 24, the observation lens 31b of the fluorescent light image pickup unit 31B is disposed such that the line a connecting the center $O_2$ of the observation lens 31b and the center $O_1$ of the observation lens 31a of the normal light image pickup unit 31A is deviated by the predetermined angle θ2 in the down bending direction of the bending portion 16 with respect to the arrow line AR which is the spouting direction of the liquid such as distilled water spouted from the spouting port 60a of the air/water feeding nozzle 60.

Accordingly, the observation lens 31b which is located further from the air/water feeding nozzle 60 than the observation lens 31a on the distal end surface of the distal end cover 24 is efficiently sprayed with the liquid such as distilled water flown down lower to the down bending direction side than the spouting direction due to the influence of gravitational force, and thereby cleaned to be a clean state. As a result, the excellent observation field of view is ensured. Furthermore, the observation lens 31b is also efficiently sprayed with the gas or air such as air or distilled water of which flow direction is changed to the down bending direction side due to the suction, and thereby cleaned to be a clean state and the excellent observation field of view is ensured.

In addition, in the endoscope 2 inserted in a body cavity of a patient, filth and the like are attached to the insertion portion 11. To the distal end surface of the distal end cover 24, in particular, the filth and the like are easily attached, because the distal end surface is an approximately vertical surface with respect to the insertion direction. Therefore, it is desirable that the observation lens 31a of the normal light image pickup unit 31A and the observation lens 31b of the fluorescent light image pickup unit 31B are surely cleaned of the attached filth and the like in order to ensure the observation field of view of the respective lenses.

In general, in an observation using the endoscope 2, the normal light observation is performed more frequently compared with the fluorescent light observation. Therefore, it is desirable to ensure the excellent observation field of view and a sufficient amount of received light in the normal light observation. The normal light image pickup unit 31A of the present embodiment is provided near the center of the distal end surface of the distal end portion 15, and is provided with the observation lens 31a having a larger lens diameter (diameter as the outer diameter) than that (diameter as the outer diameter) of the observation lens 31b for guiding light incident on the fluorescent light image pickup unit 31B for image pickup, thereby ensuring the excellent observation field of view and the sufficient amount of received light.

The endoscope of the present embodiment, in particular, has an enlargement function, so that a plurality of lens groups 32A to 32D are required so as to suppress aberration at the time of telephotographing/zooming. As a result, the light beam height becomes higher, which leads to the larger lens diameter (diameter as the outer diameter).

In other words, the observation lens 31a has the larger lens diameter (diameter as the outer diameter) than that of the observation lens 31b, that is, has a larger outer surface area, and condenses the incident light on the image pickup device 33 of the normal light image pickup unit 31A provided on an image forming side of the incident light.

Moreover, as for the gas or the liquid such as air or distilled water spouted from the spouting port 60a of the air/water feeding nozzle 60, spouting force thereof is larger on the side closer to the spouting port 60a, and as going further side of the spouting direction, the spouting force becomes smaller and the density becomes lower by diffusion.

In view of such a circumstance, as shown in FIG. 11, in the endoscope 2 of the present embodiment, the observation lens 31a of the normal light image pickup unit 31A having a larger lens diameter (diameter as the outer diameter) than that (diameter as the outer diameter) of the observation lens 31b of the fluorescent light image pickup unit 31B is disposed at a position closer to the air/water feeding nozzle 60 on the distal end surface of the distal end cover 24. Note that, as described above, the whole outer surface of the observation lens 31a is contained in the gas/liquid spouting range A to which air or distilled water is spouted from the spouting port 60a of the air/water feeding nozzle 60.

With such a configuration, the endoscope 2 has at the position closer to the air/water feeding nozzle 60 the observation lens 31a having the large lens diameter (diameter as the outer diameter) to which body fluid, filth, and the like are easily attached, thereby improving the cleaning efficiency without being subject to the influence due to a decrease in the spouting force and the density of the gas or fluid such as air or distilled water spouted from the spouting port 60a.

Note that, in the endoscope 2 of the present embodiment, as described above, the air/water feeding nozzle 60, the observation lens 31a of the normal light image pickup unit 31A, and the observation lens 31b of the fluorescent light image pickup unit 31B are almost linearly juxtaposed on the distal end surface of the distal end cover 24 shown in FIG. 12. In addition, on the distal end surface of the distal end cover 24, no other components are provided on the arrow line AR which is the spouting direction of the gas or liquid such as air or distilled water spouted from the spouting port 60a of the air/water feeding nozzle 60.

That is, on the arrow line AR, no other components are provided at an area from the observation lens 31b of the fluorescent light image pickup unit 31B to the distal end surface on the outer circumferential side of the distal end cover 24.

With such a configuration, the gas or liquid which has been used for cleaning the filth and the like attached to the respective observation lenses 31a, 31b flows to an outer edge portion of the distal end cover 24 in the arrow line AR direction as the spouting direction, without flowing toward the other components. As a result, the distal end surface of the distal end cover 24 of the endoscope 2 is surely cleaned, when the gas or liquid such as air or distilled water is spouted from the air/water feeding nozzle 60.

Next, with reference to FIGS. 12, 13, and 14, detailed description will be made on dispositions of the two illumination lenses 25a, 25b, the aperture portion 26 of the treatment instrument channel 19, and the aperture portion 27 of the forward water-feeding channel 20, which are provided on the distal end cover 24.

As described above, on the distal end surface of the distal end cover 24, two illumination lenses 25a, 25b are disposed at the positions in the left/right bending direction, respectively, so as to sandwich the observation lens 31a of the normal light image pickup unit 31A which is provided at near the center of the distal end surface. Furthermore, on the distal end surface of the distal end cover 24, the aperture portion 26 of the treatment instrument channel 19 and the aperture portion 27 of the forward water-feeding channel 20 are disposed at a position on the lower left side of the observation lens 31a and at a position on the upper right side of the observation lens 31a, respectively. In other words, the illumination lenses 25a and 25b configuring the illumination optical systems are respectively disposed such that the observation lens 31a of the normal light image pickup unit 31A approximately lines up on a straight line connecting the centers $O_3$ and $O_4$ of the illumination lenses 25a and 25b.

Figure 14:
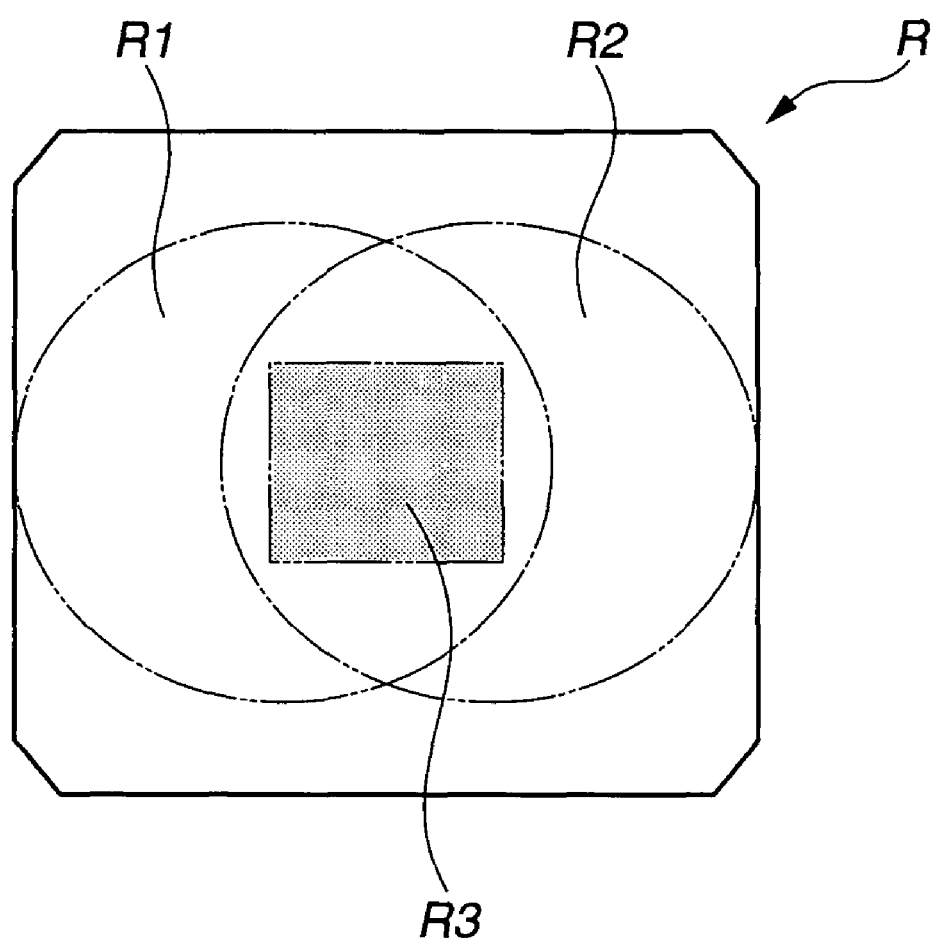
FIG. 14 is a pattern view showing an irradiation range of an illumination optical system when the distal end portion of the endoscope in FIG. 1 is inserted in a body cavity.

In a case where the distal end portion 15 on which the illumination lenses 25a and 25b are disposed at the above described positions is inserted in the body cavity, for example, as shown in FIG. 14, in a field of view area R of the observation lens 31a as the endoscope image displayed on the monitor 5, an area brightly lighted with the irradiation light emitted from the illumination lens 25a configuring the illumination optical system and an area brightly lighted with the irradiation light emitted from the illumination lens 25b configuring the illumination optical system are shown as areas R1 and R2 in a pattern view, respectively. Accordingly, the area where the area R1 and the area R2 overlap each other is illuminated with the irradiation lights emitted from both of the illumination lenses 25a and 25b. In addition, in a case where the area in the endoscope image displayed on the monitor 5 which can be displayed in an enlarged manner by the operation of the zooming operation lever, not shown, by the user is an area R3 as a part of the field of view area R of the observation lens 31a, as shown in FIG. 14, for example, the area R3 is included inside of the area where the area R1 and the area R2 overlap each other. In other words, the observation lens 31a is provided sandwiched between the illumination lenses 25a and 25b such that entirety of the area R3 which can be displayed in an enlarged manner by the normal light image pickup unit 31A is included inside of the area where the area R1 and the area R2 overlap each other.

Therefore, when the image is displayed in an enlarged manner, the user can observe a diseased part in the area R3 in a state where the diseased part is illuminated with the irradiation lights emitted from both of the illumination lenses 25a and 25b, that is, in a state where the diseased part is illuminated with the irradiation light in an amount approximately the same as that in a non-enlarged display.

In addition, as shown in FIG. 12, the aperture portion 26 of the treatment instrument channel 19 and the aperture portion 27 of the forward water-feeding channel 20 are provided on the distal end surface of the distal end cover 24 such that the entireties of the hole surfaces thereof are positioned outside of the gas/liquid spouting range A into which gas or liquid such as air or distilled water is spouted to diffuse from the spouting port 60a of the air/water feeding nozzle 60.

Figure 13:
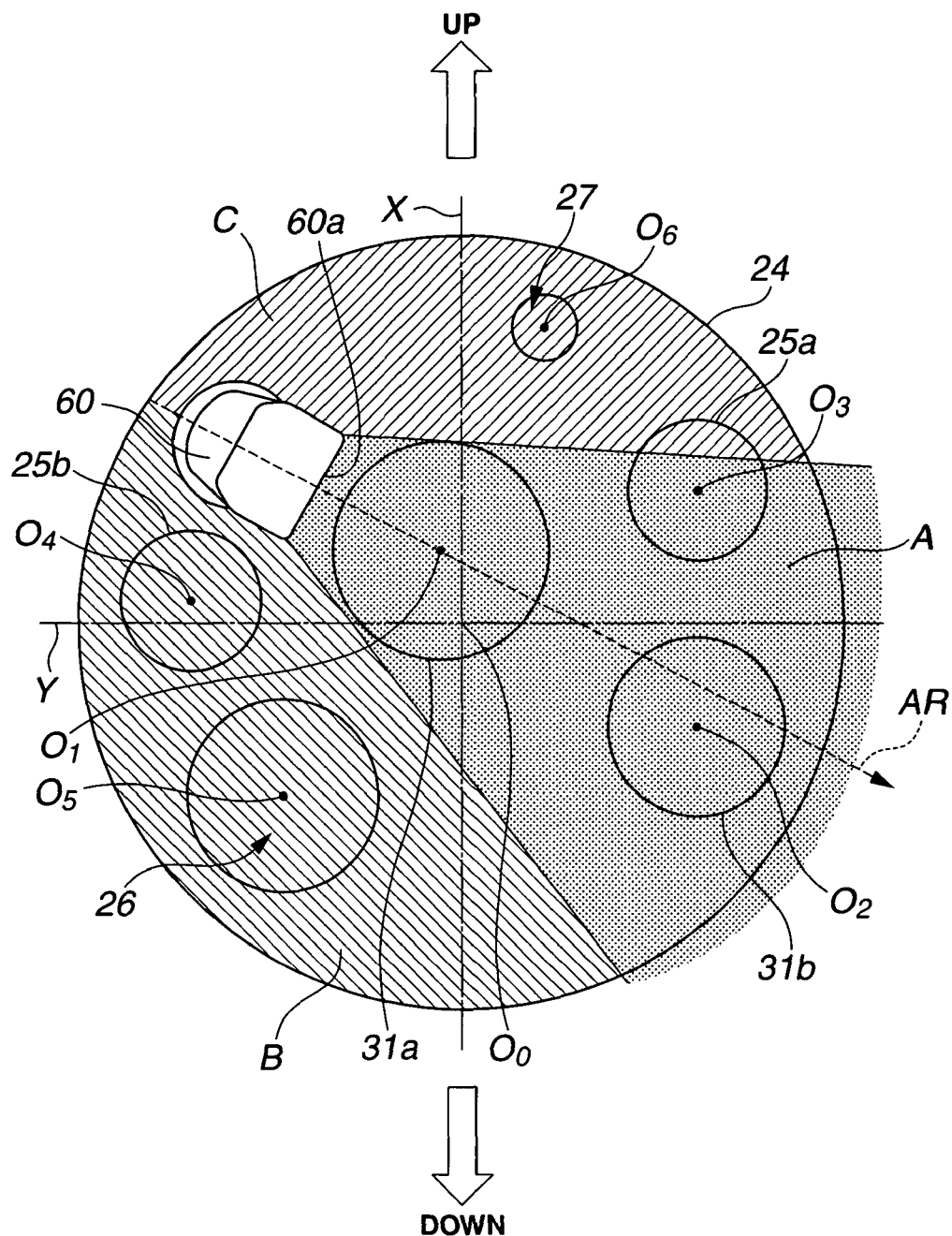
FIG. 13 is a plan view, which is different from FIGS. 4 and 12, showing the distal end cover of the endoscope in FIG. 1 viewed from the front.

In detail, as shown in FIG. 13, the aperture portion 26 of the treatment instrument channel 19 is disposed in an area B on the distal end surface of the distal end cover 24 which is an area at the lower part of the distal end surface of the distal end cover 24 when dividing the distal end surface into two parts along the arrow line AR which shows the spouting direction of the gas or liquid such as air or distilled water spouted from the spouting port 60a of the air/water feeding nozzle 60, and which is exclusive of the gas/liquid spouting range A.

In addition, the aperture portion 27 of the forward water-feeding channel 20 is disposed in an area C on the distal end surface of the distal end cover 24 which is an area at the upper part of the distal end surface of the distal end cover 24 when dividing the distal end surface into two parts along the arrow line AR, and which is exclusive of the gas/liquid spouting range A.

In other words, the respective aperture portions 26, 27 are disposed on the distal end surface of the distal end cover 24 at approximately symmetrical positions with respect to the arrow line AR showing the spouting direction of gas or liquid such as air or distilled water, respectively. That is, the respective aperture portions 26, 27 are disposed at the positions on the distal end surface of the distal end cover 24 such that the center $O_5$ of the aperture portion 26 and the center $O_6$ of the aperture portion 27 are separated from each other by a predetermined distance.

As described above, in the endoscope 2 of the present embodiment, the aperture portion 26 of the treatment instrument channel 19 and the aperture portion 27 of the forward water-feeding channel 20 are disposed outside of the gas/liquid spouting range A of the air/water feeding nozzle 60 on the distal end surface of the distal end cover 24. Therefore, in the endoscope 2 of the present embodiment, the gas or liquid such as air or distilled water spouted from the air/water feeding nozzle 60 is prevented from flowing into the respective aperture portions 26, 27.

This enables the gas or liquid such as air or distilled water spouted from the air/water feeding nozzle 60 to be surely sprayed onto the further side observation lens 31*b* of the fluorescent light image pickup unit 31B. As a result, the observation lens 31*b* of the fluorescent light image pickup unit 31B is surely and efficiently sprayed with the gas or liquid and cleaned to be a clean state, thereby ensuring the excellent observation field of view.

In addition, the respective aperture portions 26, 27 are disposed on the distal end surface of the distal end cover 24 such that the respective centers $O_5$, $O_6$ are separated from each other by a predetermined distance. With such a configuration, when spouting the liquid such as distilled water from the aperture portion 27 of the forward water-feeding channel 20 while performing suctioning action through the aperture portion 26 of the treatment instrument channel 19, the endoscope 2 can spout the liquid toward the diseased part in the body cavity without being subject to influence of suction force toward the aperture portion 26. That is, the endoscope 2 of the present invention has a configuration in which the spouting direction of the liquid spouted from the aperture portion 27 is not disturbed by the suction force from the aperture portion 26.

The endoscope 2 of the present invention having the above-described various features (effects) includes on the distal end surface of the distal end cover 24 the air/water feeding nozzle 60, the observation lens 31*a* of the normal light image pickup unit 31A, and the observation lens 31*b* of the fluorescent light image pickup unit 31B which are approximately linearly disposed. Accordingly, in the endoscope 2 of the present embodiment, gas or liquid is sprayed from one air/water feeding nozzle 60 onto the outer surface of the respective observation lenses 31*a*, 31*b* and keep the lenses in a clean state, thereby ensuring the excellent observation field of view.

Note that, the afore-mentioned special light observation is not limited to the fluorescent light observation, but may be an enlarged observation for obtaining an enlarged observation image as a special light observation image, in which the image can be enlarged to a high enlargement magnification compared with the normal light observation image by means of an enlarging optical system having an enlargement magnification of a histological level for observing a cell or gland structure (desirably equal to or more than 100 times level enlargement magnification).

Note that the present invention is not limited to the above-described embodiment, and various changes thereof could be made without departing from the spirit or scope of the invention.

What is claimed is:

1. An endoscope insertion portion comprising:
an insertion portion including a distal end surface;
a first image pickup portion including a first optical member for introducing light from a subject, the first optical member being provided on the distal end surface;
a second image pickup portion configured to obtain an observation image having an observation magnification in accordance with a zooming operation, including a second optical member for introducing light from the subject, the second optical member being provided on the distal end surface;
a first illumination optical system having a first center, the first illumination optical system being provided on the distal end surface; and
a second illumination optical system having a second center, the second illumination optical system being provided on the distal end surface such that the second optical member is disposed to approximately line up on a straight line connecting the first center and the second center, wherein
the second optical member is more frequently used for observation than the first optical member, the second optical member is disposed near an approximate center of the distal end surface, and the second optical member has an outer surface area larger than that of the first optical member; and
a region of the observation image obtained by the second image pickup portion, the region being capable of being displayed in an enlarged manner in accordance with the zooming operation, the region is provided where illumination lights respectively emitted from the first illumination optical system and the second illumination optical system overlap each other.

2. The endoscope insertion portion according to claim 1, wherein the second image pickup portion is for obtaining a normal light observation image.

3. An endoscope insertion portion comprising:
an insertion portion including a distal end portion and a bending portion at a distal end part, the bending portion being bendable in a first direction approximately coincident with an up/down direction of a monitor screen on which an endoscope image is displayed;
a first image pickup portion for obtaining a first observation image;
a second image pickup portion for obtaining a second observation image capable of being displayed in an enlarged manner in accordance with a zooming operation;
a first observation optical system for condensing light incident on the first image pickup portion, the first observation optical system being disposed on the distal end portion;
a second observation optical system for condensing light incident on the second image pickup portion, the second observation optical system being disposed on the distal end portion;
a lens provided to the second image pickup portion and capable of being advanced or retracted with respect to a photographing optical axis direction of the second image pickup portion in accordance with the zooming operation;

two illumination optical systems for emitting illumination light supplied from an illumination portion, the two illumination optical systems being disposed on the distal end portion; and an air/water feeding portion approximately lined up on a straight line connecting centers of the respective first observation optical system and the second observation optical system on the distal end surface of the distal end portion, the air/water feeding portion including a spouting direction having a first angle with respect to the first direction so as to be separated by a predetermined distance from an axis in the first direction passing through near a center of the distal end surface, the spouting direction being a direction in which gas or liquid is spouted onto outer surfaces of the first observation optical system and the second optical system from a spouting port disposed on the distal end surface, wherein, the second observation optical system is more frequently used for observation than the first observation optical system, the second observation optical system is disposed near an approximate center of the distal end surface, and the second observation optical system has an outer surface area larger than that of the first observation optical system;

on the distal end surface, the two illumination optical systems are respectively disposed such that the second observation optical system approximately lines up on a straight line connecting respective centers of the two illumination systems; and a region of the second observation image obtained by the second image pickup portion, the region being capable of being displayed in an enlarged manner in accordance with the zooming operation, the region is provided where illumination lights respectively emitted from the two illumination optical systems overlap each other.

4. The endoscope insertion portion according to claim 3, wherein the second image pickup portion is for obtaining a normal light observation image.

5. The endoscope insertion portion according to claim 3, wherein the first image pickup portion is for obtaining a special light observation image as a first observation image, and the second image pickup portion is for obtaining a normal light observation image as a second observation image.

6. The endoscope insertion portion according to claim 5, wherein the special light observation image is a fluorescent light observation image.

7. The endoscope insertion portion according to claim 5, wherein the special light observation image is an enlarged observation image as compared to the normal light observation image.

* * * * *